United States Patent [19]
O'Reilly et al.

[11] Patent Number: 5,733,876
[45] Date of Patent: Mar. 31, 1998

[54] METHOD OF INHIBITING ANGIOGENESIS

[75] Inventors: Michael S. O'Reilly, Winchester; M. Judah Folkman, Brookline, both of Mass.

[73] Assignee: The Children's Medical Center Corporation

[21] Appl. No.: 451,932

[22] Filed: May 26, 1995

Related U.S. Application Data

[62] Division of Ser. No. 248,629, Apr. 26, 1994, Pat. No. 5,639,725.

[51] Int. Cl.$^6$ .................... A61K 38/17; A61K 38/46; C07K 14/435
[52] U.S. Cl. .................. 514/12; 424/94.64; 530/350; 530/380
[58] Field of Search .................. 424/94.63, 94.64; 435/217; 514/2, 12, 21; 530/350, 380, 828, 829, 834

[56] References Cited

FOREIGN PATENT DOCUMENTS

WO 91/10424  7/1991  WIPO.

OTHER PUBLICATIONS

Derwent Publications, Ltd., London; JP 58-036-391 (Sankyo KK) Mar. 3, 1983 (Abstract).
M. O'Reilly et al., "The Suppression of Tumor Metastases by a Primary Tumor" *Science* vol. 44, pp. 474–476; 1993.
T.E. Maione et al., "Inhibition of Angiogenesis by Recombinant Human Platelet Factor–4 and Related Peptides" *Science* vol. 247, pp. 77–79; Jan. 5,1990.
M. A. Moses et al., "Identification of an Inhibitor of Neovascularization from Cartilage" *Science* vol. 248, pp. 1408–1410; Jun. 15, 1990.
Jain, R.K. Sci. Am. 271(1): 58–65, Jul. 1994.
Curti, B.D. Clin. Rev. Oncol/Hematol. 14: 29–39, 1993.
Folkman J., Tumor angiogenesis: Therapeutic implications., *N. Engl. Jour. Med.* 285:1182 1186, 1971.
Algire GH, et al. Vascular reactions of normal and malignant tumors in vivo. I. Vascular reactions of mice to wounds and to normal and neoplastic transplants. *J. Natl. Cancer Inst.* 6:73–85, 1945.
Folkman J, et al., Tumor behavior in isolated perfused organs: In vitro growth and metastasis of biopsy material in rabbit thyroid and canine intestinal segments. *Annals of Surgery* 164:491–502, 1966.
Gimbrone, M.A., Jr. et al., Tumor growth and neovascularization: An experimental model using the rabbit cornea. *J. Natl. Cancer Institute* 52:41–427, 1974.
Gimbrone MA Jr., et al., Tumor dormancy in vivo by prevention of neovascularization. *J. Exp. Med.* 136:261–276.

Knighton D., Avascular and vascular phases of tumor growth in the chick embryo. *British J. Cancer*, 35:347–356, 1977.
Lien, W., et al., The blood supply of experimental liver metastases. II. A microcirculatory study of normal and tumor vessels of the liver with the use of perfused silicone rubber. *Surgery* 68:334–340, 1970.
Folkman J, et al., Induction of angiogenesis during the transition from hyperplasia to neoplasia. *Nature* 339:58–61, 1989.
Kim K J, et al., Inhibition of vascular endothelial growth factor–induced angiogenesis suppresses tumor growth in vivo. *Nature* 362:841–844, 1993.
Hori A, et al., Suppression of solid tumor growth by immunoneutralizing monoclonal antibody against human basic fibroblast growth factor. *Cancer Research*, 51:6180–6184, 1991.
Gross JL, et al. Modulation of solid tumor growth in vivo by bFGF. *Proc. Amer. Assoc. Canc. Res.* 31:79, 1990.
Ingber D, et al., Angioinhibins: Synthetic analogues of fumagillin which inhibit angiogenesis and suppress tumor growth. *Nature*, 48:555–557, 1990.
Weidner N, et al., Tumor angiogenesis and metastasis—correlation in invasive breast carcinoma. *N. Engl. J. Med.* 324:1–8, 1991.
Weidner N, et al., Tumor angiogenesis; A new significant and independent prognostic indicator in early–stage breast carcinoma, *J Natl. Cancer Inst.* 84:1875–1887, 1992.
Weidner N, Carroll PR, Flax J, Blumenfeld W, Folkman J. Tumor angiogenesis correlates with metastasis in invasive prostate carcinoma. *American Journal of Pathology*, 143(2):401–409, 1993.

(List continued on next page.)

*Primary Examiner*—Stephen Walsh
*Assistant Examiner*—Christine Saoud
*Attorney, Agent, or Firm*—Jones & Askew

[57] ABSTRACT

The present invention is directed to methods of inhibiting angiogenesis and methods of inhibiting endothelial cell proliferation by the administration an effective amount of angiostatin protein. The angiostatin protein is an endothelial inhibitor and is isolated from the blood of urine that is eluted as a single peak from C4-reverse phase high performance liquid chromatography. Angiostatin is a molecule comprising a protein having a molecular weight of between approximately 38 kilodaltons and 45 kilodaltons as determined by reducing polyacrylamide gel electrophoresis and having an amino acid sequence substantially similar to that of a murine plasminogen fragment beginning at amino acid number 9.8 of a murine plasminogen molecule.

15 Claims, 9 Drawing Sheets

OTHER PUBLICATIONS

Srivastava A, et al., The prognostic significance of tumor vascularity in intermediate thickness (0.76–4.0 mm thick) skin melanoma. *Amer. J. Pathol.* 133:419–423, 1988.

Nguyen M, et al., Elevated levels of an angiogenic peptide, basic fibroblast growth factor, in urine of bladder cancer patients. *J. Natl. Cancer Inst.* 85:241–242, 1993.

Robbins, K.C., "The plasminogen–plasmin enzyme system" *Hemostasis and Thrombosis, Basic Principles and Practice,* 2nd Edition, ed. by Colman, R.W. et al. J.B. Lippincott Company, pp. 340–357, 1987.

Yoshimura, T, et al., "Cloning, sequencing, and expression of human macrophage stimulating protein (MSP, MST1) confirms MSP as a member of the family of kringle proteins and locates the MSP gene on Chromosome 3" *J. Biol. Chem.,* vol. 268, No. 21, pp. 15461–15468, 1993.

Browne, M.J., et al., "Expression of recombinant human plasminogen and aglycoplasminogen in HeLa cells" Fibrinolysis vol. 5 (4). 257–260, 1991.

Brem et al., "Interstitial chemotherapy with drug polymer implants for treatment of recurrent gliomas." *J. Neurosurg.* 74:441–446 (1991).

Muthukkaruppan Vr., et al., Angiogenesis in the mouse cornea. *Science* 205:1416–1418, 1979.

Passaniti A, et al., "A simple, quantitative method for assessing angiogenesis and anti–angiogenic agents using Reconstituted basement membrane, heparin and fibroblast growth factor," *Lab. Invest.,* vol. 67, p. 519 (1992).

Folkman J., Angiogenesis and its inhibitors in "*Important Advances in Oncology*", VT DeVita, S. Hellman and S. Rosenberg, editors, J.B. Lippincott, Philadelphia 1985.

Obeso, et al., "Methods in Laboratory Investigation. A Hemangioendothelioma–derived cell line; Its use as a Model for the Study of Endothelial Cell Biology," *Lab Invest.,* 63(2), pp. 259–269, 1990.

Sotrrup–Jensen, L., et al., *Progress in Chemical Fibrinolysis and Thrombolysis,* vol. 3, Davidson, J.F., et al. eds. Raven Press, New York, p. 191 (1978).

Grant, D.S., et al., "Scatter factor induces blood vessel formation in vivo." *Proc. Natl. Acad. Sci.,* vol. 90, pp. 1937–1941 (1993).

Shi, G. et al., "Kringle Domains and Plasmin Denaturation," *Biochem. and Biophys. Res. Comm.,* vol. 178, No. 1, pp. 360–368 (1991).

Scaller, J. et al., "Structural Aspects of the Plasminogen of Various Species," *Enzyme,* vol. 40, pp. 63–69 (1988).

Wiman, B., et al., "On the Specific Interaction between the Lysine–binding sites in Plasmin and Complementary Sites in $\alpha_2$–Antiplasmin and in Fibrinogen," *Biochemica et Biophysica Acta,* 579, 142 (1979).

Mouse Plasminogen Sequence:

```
met asp his lys glu val ile leu leu phe leu leu leu leu lys
pro gly gln gly asp ser leu asp gly tyr ile ser thr gln gly
ala ser leu phe ser leu thr lys lys gln leu ala ala gly gly
val ser asp cys leu ala lys cys glu gly glu thr asp phe val
cys arg ser phe gln tyr his ser lys glu gln gln cys val ile
met ala glu asn ser lys thr ser ser ile ile arg met arg asp
val ile leu phe glu lys arg val tyr leu ser glu cys lys thr
gly ile gly asn gly tyr arg gly thr met ser arg thr lys ser
gly val ala cys gln lys trp gly ala thr phe pro his val pro
asn tyr ser pro ser thr his pro asn glu gly leu glu glu asn
tyr cys arg asn pro asp asn asp glu gln gly pro trp cys tyr
thr thr asp pro asp lys arg tyr asp tyr cys asn ile pro glu
cys glu glu glu cys met tyr cys ser gly glu lys tyr glu gly
lys ile ser lys thr met ser gly leu asp cys gln ala trp asp
ser gln ser pro his ala his gly tyr ile pro ala lys phe pro
ser lys asn leu lys met asn tyr cys his asn pro asp gly glu
pro arg pro trp cys phe thr thr asp pro thr lys arg trp glu
tyr cys asp ile pro arg cys thr thr pro pro pro pro pro ser
pro thr tyr gln cys leu lys gly arg gly glu asn tyr arg gly
thr val ser val thr val ser gly lys thr cys gln arg trp ser
glu gln thr pro his arg his asn arg thr pro glu asn phe pro
cys lys asn leu glu glu asn tyr cys arg asn pro asp gly glu
thr ala pro trp cys tyr thr thr asp ser gln leu arg trp glu
tyr cys glu ile pro ser cys glu ser ser ala ser pro asp gln
ser asp ser ser val pro pro glu glu gln thr pro val val gln
glu cys tyr gln ser asp gly gln ser tyr arg gly thr ser ser
thr thr ile thr gly lys lys cys gln ser trp ala ala met phe
pro his arg his ser lys thr pro glu asn phe pro asp ala gly
leu glu met asn tyr cys arg asn pro asp gly asp lys gly pro
trp cys tyr thr thr asp pro ser val arg trp glu tyr cys asn
leu lys arg cys ser glu thr gly gly ser val val glu leu pro
thr val ser gln glu pro ser gly pro ser asp ser glu thr asp
cys met tyr gly asn gly lys asp tyr arg gly lys thr ala val
thr ala ala gly thr pro cys gln gly trp ala ala gln glu pro
his arg his ser ile phe thr pro gln thr asn pro arg ala asp
leu glu lys asn tyr cys arg asn pro asp gly asp val asn gly
pro trp cys tyr thr thr asn pro arg lys leu tyr asp tyr cys
asp ile pro leu cys ala ser ala ser ser phe glu cys gly lys
pro gln val glu pro lys lys cys pro gly arg val val gly gly
cys val ala asn pro his ser trp pro trp gln ile ser leu arg
thr arg phe thr gly gln his phe cys gly gly thr leu ile ala
pro glu trp val leu thr ala ala his cys leu glu lys ser ser
arg pro glu phe tyr lys val ile leu gly ala his glu glu tyr
ile arg gly leu asp val gln glu ile ser val ala lys leu ile
leu glu pro asn asn arg asp ile ala leu leu lys leu ser arg
pro ala thr ile thr asp lys val ile pro ala cys leu pro ser
```

Fig. 1A

```
pro asn tyr met val ala asp arg thr ile cys tyr ile thr gly
trp gly glu thr gln gly thr phe gly ala gly arg leu lys glu
ala gln leu pro val ile glu asn lys val cys asn arg val glu
tyr leu asn asn arg val lys ser thr glu leu cys ala gly gln
leu ala gly gly val asp ser cys gln gly asp ser gly gly pro
leu val cys phe glu lys asp lys tyr ile leu gln gly val thr
ser trp gly leu gly cys ala arg pro asn lys pro gly val tyr
val arg val ser arg phe val asp trp ile glu arg glu met ar

MOUSE
HUMAN
RHESUS MONKEY
PORCINE
BOVINE val tyr leu ser glu cys lys thr gly ile gly asn gly tyr arg gly
val tyr leu ser glu cys lys thr gly asn gly lys asn tyr arg gly
val tyr leu ser glu cys lys thr gly asn gly lys asn tyr arg gly
ile tyr leu ser glu cys lys thr gly asn gly lys asn tyr arg gly
ile tyr leu leu glu cys lys thr gly asn gly gln thr tyr arg gly thr met ser arg thr lys ser gly val ala cys gln lys trp gly ala
thr met ser lys thr lys asn gly ile thr cys gln lys trp ser ser
thr met ser lys thr arg thr gly ile thr cys gln lys trp ser ser
thr thr ser lys thr lys ser gly val ile cys gln lys trp ser val
thr thr ala glu thr lys ser gly val thr cys gln lys trp ser ala thr phe pro his val pro asn tyr ser pro ser thr his pro asn glu
thr ser pro his arg pro arg phe ser pro ala thr his pro ser glu
thr ser pro his arg pro thr phe ser pro ala thr his pro ser glu
ser ser pro his ile pro lys tyr ser pro glu lys phe pro leu ala
thr ser pro his val pro lys phe ser pro glu lys phe pro leu ala gly leu glu glu asn tyr cys arg asn pro asp asn asp glu gln gly
gly leu glu glu asn tyr cys arg asn pro asp asn asp pro gln gly
gly leu glu glu asn tyr cys arg asn pro asp asn asp gly gln gly
gly leu glu glu asn tyr cys arg asn pro asp asn asp glu lys gly
gly leu glu glu asn tyr cys arg asn pro asp asn asp glu asn gly pro trp cys tyr thr thr asp pro asp lys arg tyr asp tyr cys asn
pro trp cys tyr thr thr asp pro glu lys arg tyr asp tyr cys asp
pro trp cys tyr thr thr asp pro glu glu arg phe asp tyr cys asp
pro trp cys tyr thr thr asp pro glu thr arg phe asp tyr cys asp
pro trp cys tyr thr thr asp pro asp lys arg tyr asp tyr cys asp ile pro glu cys glu glu glu cys met tyr cys ser gly glu lys tyr
ile leu glu cys glu glu glu cys met his cys ser gly glu asn tyr
ile pro glu cys glu asp glu cys met his cys ser gly glu asn tyr
ile pro glu cys glu asp glu cys met his cys ser gly glu his tyr
ile pro glu cys glu asp lys cys met his cys ser gly glu asn tyr glu gly lys ile ser lys thr met ser gly leu asp cys gln ala trp
asp gly lys ile ser lys thr met ser gly leu glu cys gln ala trp
asp gly lys ile ser lys thr met ser gly leu glu cys gln ala trp
glu gly lys ile ser lys thr met ser gly ile glu cys gln ser trp
glu gly lys ile ala lys thr met ser gly arg asp cys gln ala trp

```
asp ser gln ser pro his ala his gly tyr ile pro ala lys phe pro
asp ser gln ser pro his ala his gly tyr ile pro ser lys phe pro
asp ser gln ser pro his ala his gly tyr ile pro ser lys phe pro
gly ser gln ser pro his ala his gly tyr leu pro ser lys phe pro
asp ser gln ser pro his ala his gly tyr ile pro ser lys phe pro ser lys asn leu lys met asn tyr cys his asn pro asp gly glu pro
asn lys asn leu lys lys asn tyr cys arg asn pro asp arg glu leu
asn lys asn leu lys lys asn tyr cys arg asn pro asp gly glu pro
asn lys asn leu lys met asn tyr cys arg asn pro asp gly glu pro
asn lys asn leu lys met asn tyr cys arg asn pro asp gly glu pro arg pro trp cys phe thr thr asp pro thr lys arg trp glu tyr cys
arg pro trp cys phe thr thr asp pro asn lys arg trp glu leu cys
arg pro trp cys phe thr thr asp pro asn lys arg trp glu leu cys
arg pro trp cys phe thr thr asp pro asn lys arg trp glu phe cys
arg pro trp cys phe thr thr asp pro gln lys arg trp glu phe cys asp ile pro arg cys thr thr pro pro pro pro ser pro thr tyr
asp ile pro arg cys thr thr pro pro pro ser ser gly pro thr tyr
asp ile pro arg cys thr thr pro pro pro ser ser gly pro thr tyr
asp ile pro arg cys thr thr pro pro pro thr ser gly pro thr tyr
asp ile pro arg cys thr thr pro pro pro ser ser gly pro lys tyr gln cys leu lys gly arg gly glu asn tyr arg gly thr val ser val
gln cys leu lys gly thr gly glu asn tyr arg gly asn val ala val
gln cys leu lys gly thr gly glu asn tyr arg gly asp val ala val
gln cys leu lys gly arg gly glu asn tyr arg gly thr val ser val
gln cys leu lys gly thr gly lys asn tyr gly gly thr val ala val thr val ser gly lys thr cys gln arg trp ser glu gln thr pro his
thr val ser gly his thr cys gln his trp ser ala gln thr pro his
thr val ser gly his thr cys his gly trp ser ala gln thr pro his
thr ala ser gly his thr cys gln arg trp ser ala gln ser pro his
thr glu ser gly his thr cys gln arg trp ser glu gln thr pro his arg his asn arg th

```
thr asp ser gln leu arg trp glu tyr cys glu ile pro ser cys glu
thr asn ser gln val arg trp glu tyr cys lys ile pro ser cys asp
thr asn ser gln val arg trp glu tyr cys lys ile pro ser cys glu
thr asp ser glu val arg trp asp tyr cys lys ile pro ser cys gly
thr asn ser glu val arg trp glu tyr cys thr ile pro ser cys glu ser ser ala ser pro asp gln ser asp ser val pro pro glu glu
ser ser pro val ser thr glu gln leu ala pro thr ala pro pro glu
ser ser pro val ser thr glu pro leu asp pro thr ala pro pro glu
ser ser thr thr ser thr glu his leu asp ala pro val pro pro glu
ser ser pro leu ser thr glu arg met asp val pro val pro pro glu gln thr pro val val gln glu cys tyr gln ser asp gly gln ser tyr
leu thr pro val val gln asp cys tyr his gly asp gly gln ser tyr
leu thr pro val val gln glu cys tyr his gly asp gly gln ser tyr
gln thr pro val ala gln asp cys tyr arg gly asn gly glu ser tyr
gln thr pro val pro gln asp cys tyr his gly asn gly gln ser tyr arg gly thr ser ser thr thr ile thr gly lys lys cys gln ser trp
arg gly thr ser ser thr thr thr thr gly lys lys cys gln ser trp
arg gly thr ser ser thr thr thr thr gly lys lys cys gln ser trp
arg gly thr ser ser thr thr ile thr gly arg lys cys gln ser trp
arg gly thr ser ser thr thr ile thr gly arg lys cys gln ser trp ala ala met phe pro his arg his

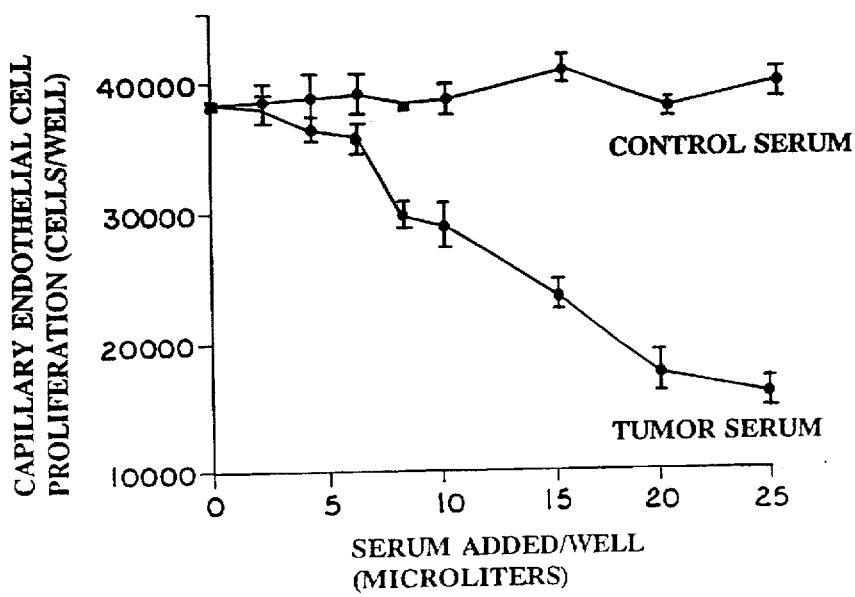
Fig_5
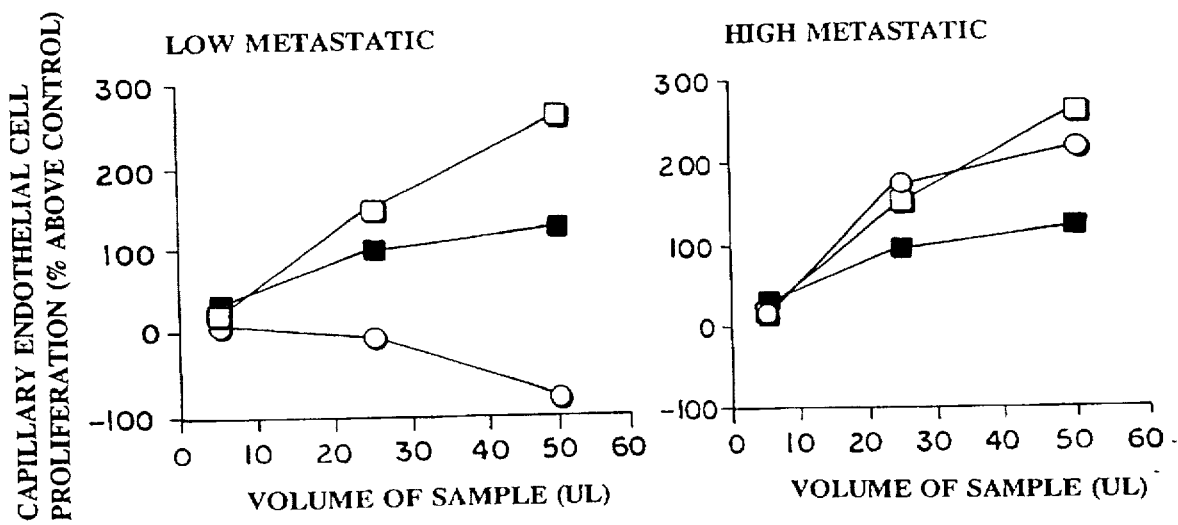
Fig_6A    Fig_6B

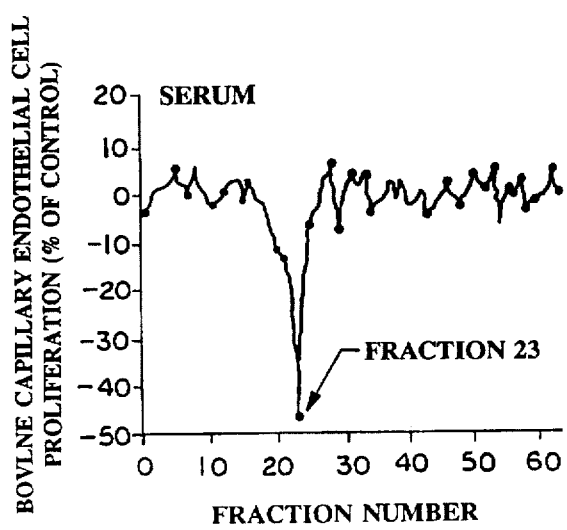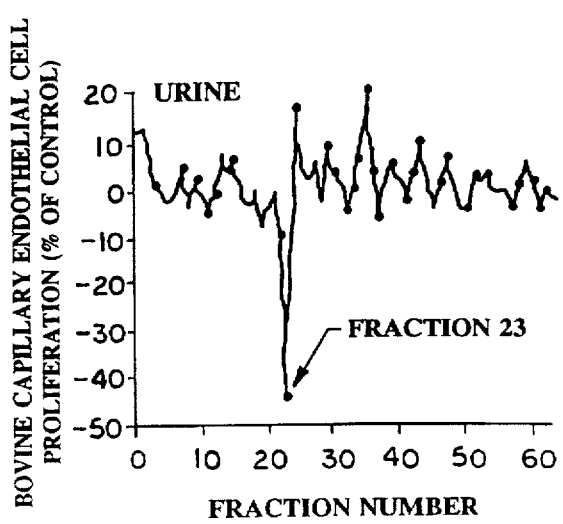
Fig_7A    Fig_7B

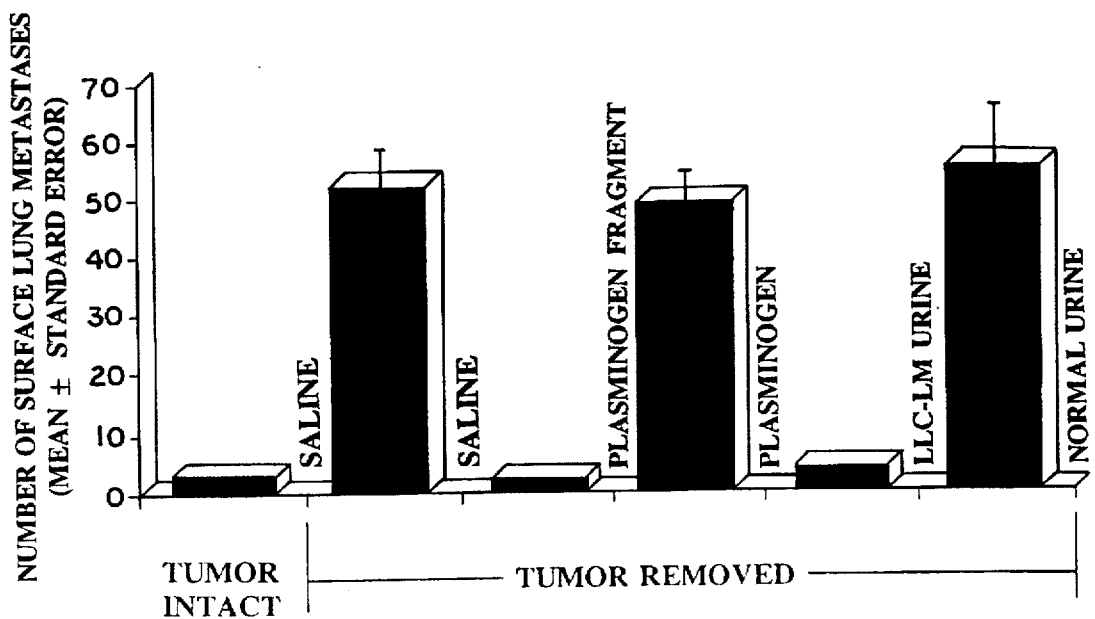
Fig_8
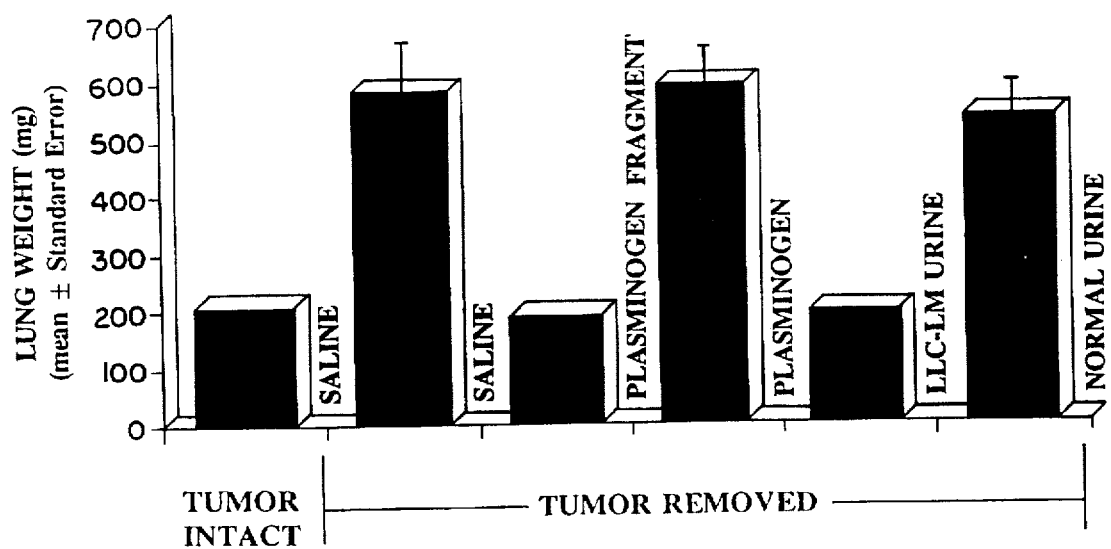
Fig_9

METHOD OF INHIBITING ANGIOGENESIS

This is a division of application Ser. No. 08/248,629, filed Apr. 26, 1994 now U.S. Pat. No. 5,639,725.

FIELD OF THE INVENTION

The present invention relates to an endothelial inhibitor, called angiostatin, which reversibly inhibits proliferation of endothelial cells. More particularly, the present invention relates to angiostatin proteins that can be isolated from body fluids such as blood or urine or can be synthesized by recombinant, enzymatic or chemical methods. The angiostatin is capable of inhibiting angiogenesis related diseases and modulating angiogenic processes. In addition, the present invention relates to diagnostic assays for the angiostatin and to antibodies that are specific for the angiostatin.

BACKGROUND OF THE INVENTION

As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" means a thin layer of flat epithelial cells that lines serous cavities, lymph vessels, and blood vessels. The term "endothelial inhibiting activity" means the capability of a molecule to inhibit angiogenesis in general and, for example, to inhibit the growth of bovine capillary endothelial cells in culture in the presence of fibroblast growth factor.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic dependent or angiogenic associated diseases.

The hypothesis that tumor growth is angiogenesis-dependent was first proposed in 1971. (Folkman J., Tumor angiogenesis: Therapeutic implications., N. Engl. Jour. Med. 285:1182 1186, 1971) In its simplest terms it states: "Once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

Examples of the indirect evidence which support this concept include:

(1) The growth rate of tumors implanted in subcutaneous transparent chambers in mice is slow and linear before neovascularization, and rapid and nearly exponential after neovascularization. (Algire G H, et al. Vascular reactions of normal and malignant tumors in vivo. I. Vascular reactions of mice to wounds and to normal and neoplastic transplants. *J. Natl. Cancer Inst.* 6:73–85, 1945)

(2) Tumors grown in isolated perfused organs where blood vessels do not proliferate are limited to 1–2 $mm^3$ but expand rapidly to >1000 times this volume when they are transplanted to mice and become neovascularized. (Folkman J, et al., Tumor behavior in isolated perfused organs: In vitro growth and metastasis of biopsy material in rabbit thyroid, and canine intestinal segments. *Annals of Surgery* 164:491–502, 1966)

(3) Tumor growth in the avascular cornea proceeds slowly and at a linear rate, but switches to exponential growth after neovascularization. (Gimbrone, M. A., Jr. et al., Tumor growth and neovascularization: An experimental model using the rabbit cornea. *J. Natl. Cancer Institute* 52:41–427, 1974)

(4) Tumors suspended in the aqueous fluid of the anterior chamber of the rabbit eye, remain viable, avascular and limited in size to <1 $mm^3$. Once they are implanted on the iris vascular bed, they become neovascularized and grow rapidly, reaching 16,000 times their original volume within 2 weeks. (Gimbrone M A Jr., et al., Tumor dormancy in vivo by prevention of neovascularization. *J. Exp. Med.* 136:261–276)

(5) When tumors are implanted on the chick embryo chorioallantoic membrane, they grow slowly during an avascular phase of >72 hours, but do not exceed a mean diameter of 0.93+0.29 mm. Rapid tumor expansion occurs within 24 hours after the onset of neovascularization, and by day 7 these vascularized tumors reach a mean diameter of 8.0+2.5 mm. (Knighton D., Avascular and vascular phases of tumor growth in the chick embryo. *British J. Cancer*, 35:347–356, 1977)

(6) Vascular casts of metastases in the rabbit liver reveal heterogeneity in size of the metastases, but show a relatively uniform cut-off point for the size at which vascularization is present. Tumors are generally avascular up to 1 mm in diameter, but are neovascularized beyond that diameter. (Lien W., et al., The blood supply of experimental liver metastases. II. A microcirculatory study of normal and tumor vessels of the liver with the use of perfused silicone rubber. *Surgery* 68:334–340, 1970)

(7) In transgenic mice which develop carcinomas in the beta cells of the pancreatic islets, pre-vascular hyperplastic islets are limited in size to <1 mm. At 6–7 weeks of age, 4–10% of the islets become neovascularized, and from these islets arise large vascularized tumors of more than 1000 times the volume of the pre-vascular islets. (Folkman J, et al., Induction of angiogenesis during the transition from hyperplasia to neoplasia. *Nature* 339:58–61, 1989)

(8) A specific antibody against VEGF (vascular endothelial growth factor) reduces microvessel density and causes "significant or dramatic" inhibition of growth of three human tumors which rely on VEGF as their sole mediator of angiogenesis (in nude mice). The antibody does not inhibit growth of the tumor cells in vitro. (Kim K J, et al., Inhibition of vascular endothelial growth factor-induced angiogenesis suppresses tumor growth in vivo. *Nature* 362:841–844, 1993)

(9) Anti-bFGF monoclonal antibody causes 70% inhibition of growth of a mouse tumor which is dependent upon secretion of bFGF as its only mediator of angiogenesis. The antibody does not inhibit growth of the tumor cells in vitro. (Hori A, et al., Suppression of solid tumor growth by immunoneutralizing monoclonal antibody against human basic fibroblast growth factor. *Cancer Research*, 51:6180–6184, 1991)

(10) Intraperitoneal injection of bFGF enhances growth of a primary tumor and its metastases by stimulating growth of capillary endothelial cells in the tumor. The tumor cells themselves lack receptors for bFGF, and bFGF is not a mitogen for the tumors cells in vitro. (Gross J L, et al. Modulation of solid tumor growth in vivo by bFGF. *Proc. Amer. Assoc. Canc. Res.* 31:79, 1990)

(11) A specific angiogenesis inhibitor (AGM-1470) inhibits tumor growth and metastases in vivo, but is much less active in inhibiting tumor cell proliferation in vitro. It inhibits vascular endothelial cell proliferation half-maximally at 4 logs lower concentration than it inhibits tumor cell proliferation. (Ingber D, et al., Angioinhibins: Synthetic analogues of fumagillin which inhibit angiogenesis and suppress tumor growth. *Nature*, 48:555–557, 1990)

There is also indirect clinical evidence that tumor growth is angiogenesis dependent.

(12) Human retinoblastomas that are metastatic to the vitreous develop into avascular spheroids which are restricted to less than 1 mm$^3$ despite the fact that they are viable and incorporate $^3$H-thymidine (when removed from an enucleated eye and analyzed in vitro).

(13) Carcinoma of the ovary metastasizes to the peritoneal membrane as tiny avascular white seeds (1–3 mm$^3$). These implants rarely grow larger until one or more of them becomes neovascularized.

(14) Intensity of neovascularization in breast cancer (Weidner N, et al., Tumor angiogenesis correlates with metastasis in invasive breast carcinoma. *N. Engl. J. Med.* 324:1–8, 1991, and Weidner N, et al., Tumor angiogenesis: A new significant and independent prognostic indicator in early-stage breast carcinoma, *J Natl. Cancer Inst.* 84:1875–1887, 1992) and in prostate cancer (Weidner N, Carroll P R, Flax J, Blumenfeld W, Folkman J. Tumor angiogenesis correlates with metastasis in invasive prostate carcinoma. *American Journal of Pathology*, 143(2):401–409, 1993) correlates highly with risk of future metastasis.

(15) Metastasis from human cutaneous melanoma is rare prior to neovascularization. The onset of neovascularization leads to increased thickness of the lesion and an increasing risk of metastasis. (Srivastava A, et al., The prognostic significance of tumor vascularity in intermediate thickness (0.76–4.0 mm thick) skin melanoma. *Amer. J. Pathol.* 133:419–423, 1988)

(16) In bladder cancer, the urinary level of an angiogenic peptide, bFGF, is a more sensitive indicator of status and extent of disease than is cytology. (Nguyen M, et al., Elevated levels of an angiogenic peptide, basic fibroblast growth factor, in urine of bladder cancer patients. *J. Natl. Cancer Inst.* 85:241–242, 1993)

Thus, it is clear that angiogenesis plays a major role in the metastasis of a cancer. If this angiogenic activity could be repressed or eliminated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

What is needed therefore is a composition and method which can inhibit the unwanted growth of blood vessels, especially into tumors. The composition should be able to overcome the activity of endogenous growth factors in premetastatic tumors and prevent the formation of the capillaries in the tumors thereby inhibiting the growth of the tumors. The composition, and antibodies specific to the composition, should also be able to modulate the formation of capillaries in other angiogenic processes, such as wound healing and reproduction. Finally, the composition and method for inhibiting angiogenesis should preferably be non-toxic and produce few side effects.

SUMMARY OF THE INVENTION

In accordance with the present invention, compositions and methods are provided that are effective in inhibiting unwanted angiogenesis, especially angiogenesis related to tumor growth. The present invention includes a protein, which has been named "angiostatin", defined by its ability to overcome the angiogenic activity of endogenous growth factors such as bFGF, in vitro. Angiostatin comprises a protein having a molecular weight of between approximately 38 kilodaltons and 45 kilodaltons as determined by reducing polyacrylamide gel electrophoresis and having an amino acid sequence substantially similar to that of a fragment of murine plasminogen beginning at amino acid number 98 of an intact murine plasminogen molecule.

The amino acid sequence of angiostatin varies slightly between species. For example, in human angiostatin the amino acid sequence is substantially similar to the sequence of the above described murine plasminogen fragment, although an active human angiostatin sequence may start at either amino acid number 97 or 99 of an intact human plasminogen amino acid sequence. Further, human plasminogen has similar anti-angiogenic activity as shown in a mouse tumor model. It is to be understood that the number of amino acids in the active angiostatin molecule may vary and all amino acid sequences that have endothelial inhibiting activity are contemplated as being included in the present invention.

The present invention provides methods and compositions for treating diseases and processes mediated by undesired and uncontrolled angiogenesis by administering to a human or animal a composition comprising a substantially purified angiostatin or angiostatin derivative in a dosage sufficient to inhibit angiogenesis. The present invention is particularly useful for treating or for repressing the growth of tumors. Administration of angiostatin to a human or animal with prevascularized metastasized tumors will prevent the growth or expansion of those tumors.

The present invention also includes diagnostic methods and kits for detecting the angiostatin in biological fluids. The diagnostic method and kit can be in any configuration well known to those of ordinary skill in the art. The present invention also includes antibodies specific for the angiostatin and antibodies that inhibit the binding of antibodies specific for the angiostatin. These antibodies can be polyclonal antibodies or monoclonal antibodies. The antibodies specific for the angiostatin can be used in diagnostic kits to detect the presence and quantity of angiostatin which is diagnostic or prognostic for the occurrence or recurrence of cancer or other disease mediated by angiogenesis. Antibodies specific for angiostatin may also be administered to a human or animal to passively immunize the human or animal against angiostatin, thereby reducing angiogenic inhibition.

The present invention also includes diagnostic methods and kits for detecting the presence and quantity of antibodies that bind angiostatin in body fluids. The diagnostic method and kit can be in any configuration well known to those of ordinary skill in the art.

Accordingly, it is an object of the present invention to provide a composition comprising an angiostatin.

It is another object of the present invention to provide a method of treating diseases and processes that are mediated by angiogenesis.

It is yet another object of the present invention to provide a diagnostic or prognostic method and kit for detecting the presence and amount of angiostatin in a body fluid.

It is yet another object of the present invention to provide a method and composition for treating diseases and processes that are mediated by angiogenesis including, but not limited to, hemangioma, solid tumors, leukemia, metastasis, telangiectasia psoriasis scleroderma, pyogenic granuloma, Myocardial angiogenesis, plaque neovascularization, cororany collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation.

It is another object of the present invention to provide a composition for treating or repressing the growth of a cancer.

It is an object of present invention to provide a method for detecting and quantifying the presence of an antibody specific for an angiostatin in a body fluid.

It is another object of the present invention to provide a method for the detection or prognosis of cancer.

It is yet another object of the present invention to provide a therapy for cancer that has minimal side effects.

These and other objects, features and advantages of the present invention will become apparent after a review of the following detailed description of the disclosed embodiments and the appended claims.

BRIEF DESCRIPTION OF THE FIGURES

FIGS. 1A and 1B show SEQ ID NO: 1, the amino acid sequence of the whole murine plasminogen.

FIGS. 2A and 2C show the beginning sequence of the angiostatin for murine (SEQ ID NO: 2) and compares the murine sequence with corresponding human (SEQ ID NO: 3), Rhesus monkey (SEQ ID NO: 4), porcine (SEQ ID NO: 5) and bovine (SEQ ID NO: 6) plasminogen peptide fragments. The mouse sequence is listed first, followed by human, Rhesus, porcine and bovine.

FIG. 5 shows dose response curve for serum derived from mice bearing Lewis lung carcinoma (LLC-Low) versus serum from normal mice. Bovine capillary endothelial cells were assayed in a bFGF-driven 72-hour proliferation assay.

FIGS. 6A and 6B show that both low (FIG. 6A) and high (FIG. 6B) metastatic tumors contain endothelial mitogenic activity in their ascites, but only the low metastatic tumor line has endothelial inhibitory activity in the serum.

FIGS. 7A and 7B show a Reverse Phase Chromatography profile of partially purified serum (FIG. 7A) or urine (FIG. 7B) from tumor-bearing animals.

FIG. 8 shows surface lung metastases after the 13 day treatment of mice with intact plasminogen molecule, active fraction from a lysine binding site I preparation, concentrated urine from tumor bearing mice and concentrated urine from normal mice.

FIG. 9 shows lung weight after the 13 day treatment of mice with intact plasminogen molecule, active fraction from lysine binding site I preparation, concentrated urine from tumor bearing mice and concentrated urine from normal mice.

DETAILED DESCRIPTION

Figure 3A:
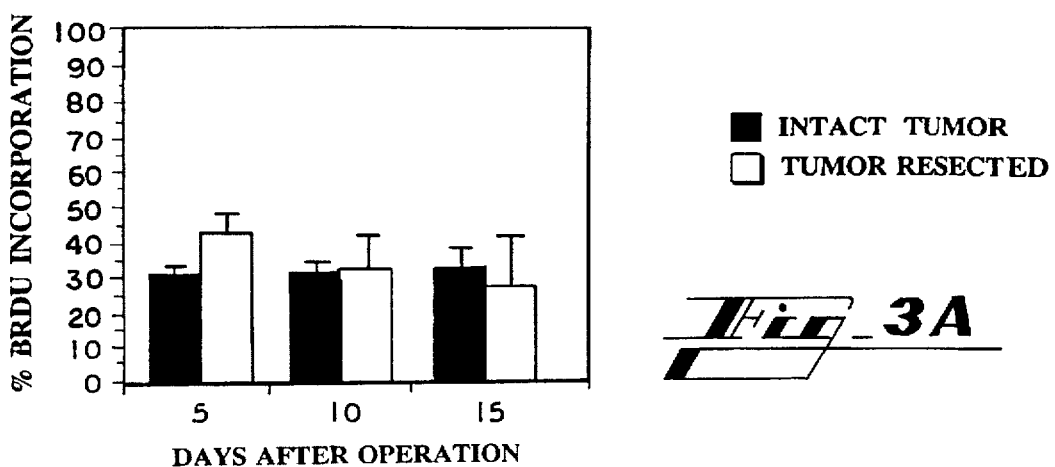
FIG. 3A shows BrdU labeling index of tumor cells in the lung in the presence or absence of a primary tumor.

The present invention includes compositions and methods for the treatment of diseases and processes that are mediated by or associated with angiogenesis. The composition is angiostatin, which can be isolated from body fluids including, but not limited to, serum, urine and ascites, or synthesized by chemical or biological methods (e.g. cell culture, recombinant gene expression, and in vitro enzymatic catalysis of plasminogen or plasmin to yield active angiostatin). Recombinant techniques include gene amplification from DNA sources using the polymerase chain reaction (PCR), and gene amplification from RNA sources using reverse transcriptase/PCR. Angiostatin inhibits the growth of blood vessels into tissues such as unvascularized or vascularized tumors. The present invention includes a protein that has a molecular weight of approximately 38 to 45 kilodaltons that is capable of overcoming the angiogenic activity of endogenous growth factors such as bFGF, in vitro. Angiostatin is a protein having a molecular weight of between approximately 38 kilodaltons and 45 kilodaltons as determined by reducing polyacrylamide gel electrophoresis and having an amino acid sequence substantially similar to that of a murine plasminogen fragment beginning at amino acid number 98 of an intact murine plasminogen molecule. The term "substantially similar," when used in reference to angiostatin amino acid sequences, means an amino acid sequence having anti-angiogenic activity and having a molecular weight of approximately 38 kD to 45 kD, which also has a high degree of sequence homology to the peptide fragment of mouse plasminogen beginning approximately at amino acid number 98 in mouse plasminogen and weighing 38 kD to 45 kD. A high degree of homology means approximately 60% amino acid homology, suitably approximately 70% amino acid homology, and desirably approximately 80% amino acid homology.

The amino acid sequence of the complete murine plasminogen molecule is shown in FIGS. 1A and 1B and in SEQ ID NO: 1, The sequence for angiostatin begins approximately at amino acid 98. Active human angiostatin may start at either amino acid 97 or 99 of the intact human plasminogen molecule. The amino acid sequence of the first 339 amino acids of angiostatin from mouse is shown in FIGS. 2A, 2B and 2C, (SEQ ID NO: 2), and is compared with the sequences of corresponding plasminogen peptide fragments from human (SEQ ID NO: 3, Rhesus monkey (SEQ ID NO: 4), porcine (SEQ ID NO: 5) and bovine (SEQ ID NO: 6) plasminogen. Given that these sequences are identical in well over 50% of their amino acids, it is to be understood that the amino acid sequence of the angiostatin is substantially similar among species. The total number of amino acids in the angiostatin is not known precisely but is defined by the molecular weight of the active molecule. The amino acid sequence of the angiostatin of the present invention may vary depending upon from which species the plasminogen molecule is derived. Thus, although the angiostatin of the present invention that is derived from human plasminogen has a slightly different sequence than angiostatin derived from mouse it has anti-angiogenic activity as shown in a mouse tumor model.

Angiostatin has been shown to be capable of inhibiting the growth of endothelial cells in vitro. Angiostatin does not inhibit the growth of cell lines derived from other cell types. Specifically, angiostatin has no effect on Lewis lung carcinoma cell lines, mink lung epithelium, 3T3 fibroblasts, bovine aortic smooth muscle cells, bovine retinal pigment epithelium, MDCk (canine renal epithelium, WI38 cells (human fetal lung fibroblasts) EFN cells (murine fetal fibroblasts) and LM cells (murine connective tissue).

Angiostatin has a specific three dimensional conformation that is defined by the kringle region of the plasminogen molecule. (Robbins, K. C., "The plasminogen-plasmin enzyme system" *Hemostasis and Thrombosis, Basic Principles and Practice*, 2nd Edition, ed. by Colman, R. W. et al. J. B. Lippincott Company, pp. 340–357, 1987) There are five such kringle regions, which are conformationally related motifs and have substantial sequence homology, in the $NH_2$ terminal portion of the plasminogen molecule. The three dimensional conformation of angiostatin is believed to encompass plasminogen kringles 1 through 3 and a part of kringle 4. Each kringle region of the plasminogen molecule contains approximately 80 amino acids and contains 3 disulfide bonds. This cysteine motif is known to exist in other biologically active proteins. These proteins include, but are not limited to, prothrombin, hepatocyte growth fact/scatter factor and macrophage stimulating protein. (Yoshimura, T, .et al., "Cloning, sequencing, and expression of human macrophage stimulating protein (MSP, MST1) confirms MSP as a member of the family of kringle proteins and locates the MSP gene on Chromosome 3" *J. Biol. Chem..*, Vol. 268, No. 21, pp. 15461–15468, 1993) It is contemplated that any isolated protein or peptide having a three dimensional kringle-like conformation or cysteine motif that has anti-angiogenic activity in vivo, is part of the present invention.

The present invention also includes the detection of the angiostatin in body fluids for the purpose of diagnosis or prognosis of diseases such as cancer. The present invention also includes methods of treating or preventing angiogenic diseases and processes including, but not limited to, arthritis and tumors by stimulating the production of angiostatin, and/or by administering substantially purified angiostatin to a patient. It is to be understood that the angiostatin can be animal or human in origin. Angiostatin can also be produced synthetically by chemical reaction or by recombinant techniques. Angiostatin can also be produced by enzymatically cleaving isolated plasminogen or plasmin to generate peptides having anti-angiogenic activity.

Passive antibody therapy using antibodies that specifically bind angiostatin can be employed to modulate angiogenic-dependent processes such as reproduction, development, and wound healing and tissue repair.

Angiostatin can be isolated on an HPLC C4 column (see Table 3). The angiostatin protein is eluted at 30 to 35% in an acetonitrile gradient. On a sodium dodecyl sulfate polyacrylamide gel electrophoresis (PAGE) gel under reducing conditions, the protein band with activity eluted as a single peak at approximately 38 kilodaltons.

The inventors have shown that a growing primary tumor is associated with the release into the blood stream specific inhibitor(s) of endothelial cell proliferation, including angiostatin which can suppress angiogenesis within a metastasis and thereby inhibit the growth of the metastasis itself. The source of the angiostatin associated with the primary tumor is not known. The compound may be produced by degradation of plasminogen by a specific protease, or angiostatin could be produced by expression of a specific gene coding for angiostatin. The angiogenic phenotype of a primary tumor depends on production of angiogenic peptides in excess of endothelial cell inhibitors which are elaborated by normal cells, but are believed to be down-regulated during transformation to neoplasia. While production of angiostatin may be down-regulated in an individual minor cell relative to production by its parent, the total inhibitor elaborated by the whole tumor may be sufficient to enter the circulation and suppress endothelial growth at remote sites of micrometastases. Angiostatin remains in the circulation for a significantly longer time than the angiogenic peptide(s) released by a primary tumor. Thus, the angiogenic peptides appear to act locally, whereas endothelial cell inhibitor acts globally, circulating in the blood with relatively long half-lives. The half-life of the angiostatin is approximately 12 hours to 5 days.

Although not wanting to be bound by the following hypothesis, it is believed that when a tumor becomes angiogenic it releases one or more angiogenic peptides (e.g., aFGF, bFGF, VEGF, IL-8, GM-CSF, etc.), which act locally, target endothelium in the neighborhood of a primary tumor from an extravascular direction, and do not circulate (or circulate with a short half-life). These angiogenic peptides must be produced in an amount sufficient to overcome the action of endothelial cell inhibitor (inhibitors of angiogenesis) for a primary tumor to continue to expand its population. Once such a primary tumor is growing well, it continues to release endothelial cell inhibitors into the circulation. According to this hypothesis, these inhibitors act at a distance from the primary tumor, target capillary endothelium of a metastasis from an intravascular direction, and continue to circulate. Thus, just at the time when a remote metastasis might begin to initiate angiogenesis, the capillary endothelium in its neighborhood could be swamped by incoming angiostatin.

Once a primary tumor has reached sufficient size to cause angiostatin to be released continuously into the circulation, it is difficult for a second minor implant (or a micrometastasis) to initiate or increase its own angiogenesis. If a second tumor implant (e.g., into the subcutaneous space, or into the cornea, or intravenously to the lung) occurs at the same time, or shortly after the primary tumor is implanted, the primary tumor will not be able to suppress the secondary tumor (because angiogenesis in the secondary tumor will already be well underway). If two tumors are implanted simultaneously (e.g., in opposite flanks), the inhibitors may have an equivalent inhibiting effect on each other.

The angiostatin of the present invention can be:
  (i) Administered to tumor-bearing humans or animals as anti-angiogenic therapy.
  (ii) Monitored in human or animal serum or urine as prognostic markers.
  (iii) Used as the basis to analyze serum and urine of cancer patients for similar angiostatic molecules.

Angiostatin can be used therapeutically as a long-term anti-metastatic therapy Angiostatin can also be used to develop methods and kits for measuring the concentration in a body fluid such as urine or blood. By measuring the concentration of the angiostatin in a body fluid, such as blood or urine, one can diagnose a cancer or determine the prognosis of the disease.

It is contemplated as part of the present invention that angiostatin can be isolated from a body fluid such as blood or urine of patients or the angiostatin can be produced by recombinant DNA methods or synthetic peptide chemical methods that are well known to those of ordinary skill in the art. Protein purification methods are well known in the art and a specific example of a method for purifying angiostatin, and assaying for inhibitor activity is provided in the examples below. Isolation of human endogenous angiostatin is accomplished using similar techniques.

One example of a method of producing angiostatin using recombinant DNA techniques entails the steps of (1) identifying and purifying an angiostatin as discussed above, and as more fully described below, (2) determining the N-terminal amino acid sequence of the purified inhibitor, (3) synthetically generating a DNA oligonucleotide probe that corresponds to the N-terminal amino acid sequence, (4) generating a DNA gene bank from human or other mammalian DNA, (5) probing the gene bank with the DNA oligonucleotide probe, (6) selecting clones that hybridize to the oligonucleotide, (7) isolating the inhibitor gene from the clone, (8) inserting the gene into an appropriate vector such as an expression vector, (9) inserting the gene-containing vector into a microorganism or other expression system capable of expressing the inhibitor gene, and (10) isolating the recombinantly produced inhibitor. The above techniques are more fully described in laboratory manuals such as "Molecular Cloning: A Laboratory Manual" Second Edition by Sambrook et al., Cold Spring Harbor Press, 1989. The DNA sequence of human plasminogen has been published (Browne, M. J., et al., "Expression of recombinant human plasminogen and aglycoplasminogen in HeLa cells" Fibrinolysis Vol.5 (4). 257–260, 1991) and is incorporated herein by reference The gene for angiostatin may also be isolated from cells or tissue (such as tumor cells) that express high levels of angiostatin by (1) isolating messenger RNA from the tissue, (2) using reverse transcriptase to generate the corresponding DNA sequence and then (3) using PCR with the appropriate primers to amplify the DNA sequence coding for the active angiostatin amino acid sequence.

Yet another method of producing angiostatin, or biologically active fragments thereof, is by peptide synthesis. Once a biologically active fragment of an angiostatin is found using the assay system described more fully below, it can be sequenced, for example by automated peptide sequencing methods. Alternatively, once the gene or DNA sequence which codes for angiostatin is isolated, for example by the methods described above, the DNA sequence can be determined, which in turn provides information regarding the amino acid sequence. Thus, if the biologically active fragment is generated by specific methods, such as tryptic digests, or if the fragment is N-terminal sequenced, the remaining amino acid sequence can be determined from the corresponding DNA sequence.

Once the amino acid sequence of the peptide is known, the fragment can be synthesized by techniques well known in the art, as exemplified by "Solid Phase Peptide Synthesis: A Practical Approach" E. Atherton and R. C. Sheppard, IRL Press, Oxford England. Similarly, multiple fragments can be synthesized which are subsequently linked together to form larger fragments.

Angiostatin is effective in treating diseases or processes that are mediated by, or involve, angiogenesis. The present invention includes the method of treating an angiogenesis mediated disease with an effective amount of angiostatin. The angiogenesis mediated diseases include, but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. Angiostatin is useful in the treatment of disease of excessive or abnormal stimulation of endothelial cells. These diseases include, but are not limited to, intestinal adhesions, atherosclerosis, scleroderma, and hypertrophic scars, i.e., keloids. Angiostatin can be used as a birth control agent by preventing vascularization required for embryo implantation.

Angiostatin may be used in combination with other compositions and procedures for the treatment of diseases. For example, a tumor may be treated conventionally with surgery, radiation or chemotherapy combined with angiostatin and then angiostatin may be subsequently administered to the patient to extend the dormancy of micrometastases and to stabilize any residual primary tumor.

The angiostatin of the present invention also can be used to generate antibodies that are specific for the inhibitor. The antibodies can be either polyclonal antibodies or monoclonal antibodies. These antibodies that specifically bind to the angiostatin can be used in diagnostic methods and kits that are well known to those of ordinary skill in the art to detect or quantify the angiostatin in a body fluid. Results from these tests can be used to diagnose or predict the occurrence or recurrence of a cancer and other angiogenic mediated diseases.

The angiostatin also can be used in a diagnostic method and kit to detect and quantify antibodies capable of binding angiostatin. Patients that have such circulating anti-angiostatin antibodies may be more likely to develop tumors and cancers, and may be more likely to have recurrences of cancer after treatments or periods of remission.

Another aspect of the present invention is a method of blocking the action of excess endogenous angiostatin. This can be done by passively immunizing a human or animal with antibodies specific for the undesired angiostatin in the system. This treatment can be important in treating abnormal ovulation, menstruation and placentation, and vasculogenesis.

It is to be understood that the present invention is contemplated to include any derivatives of the angiostatin that have endothelial inhibitory activity. The present invention includes the entire angiostatin protein, derivatives of the angiostatin protein and biologically-active fragments of the angiostatin protein. These include proteins with angiostatin activity that have amino acid substitutions or have sugars or other molecules attached to amino acid functional groups. The present invention also includes genes that code for angiostatin and to proteins that are expressed by those genes.

The proteins and protein fragments with the angiostatin activity described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, oral, rectal or parenteral (e.g., intravenous, subcutaneous or intramuscular) mute. In addition, the angiostatin may be incorporated into biodegradable polymers allowing for sustained release of the compound, the polymers being implanted in the vicinity of where drug delivery is desired, for example, at the site of a tumor or implanted so that the angiostatin is slowly released systemically. The biodegradable polymers and their use are described, for example, in detail in Brem et al., *J. Neurosurg.* 74:441–446 (1991), which is hereby incorporated by reference in its entirety.

The dosage of the angiostatin of the present invention will depend on the disease state or condition being treated and other clinical factors such as weight and condition of the human or animal and the route of administration of the compound. For treating humans or animals, between approximately 0.5 mg/kilogram to 500 mg/kilogram of the angiostatin can be administered. Depending upon the half-life of the angiostatin in the particular animal or human, the angiostatin can be administered between several times per day to once a week. It is to be understood that the present invention has application for both human and veterinary use. The methods of the present invention contemplate single as well as multiple administrations, given either simultaneously or over an extended period of time.

The angiostatin formulations include those suitable for oral, rectal, ophthalmic (including intravitreal or intracameral), nasal, topical (including buccal and sublingual), vaginal or parenteral (including subcutaneous, intraperitoneal, intramuscular, intravenous, intradermal, intratracheal, and epidural) administration. The angiostatin formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or, multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Choice of an animal-tumor system in which growth of metastasis is inhibited by the primary tumor and is accelerated after removal of the primary tumor.

By screening a variety of murine tumors capable of inhibiting their own metastases, a Lewis lung carcinoma was selected in which the primary tumor most efficiently inhibited lung metastasis. Syngeneic C57BI6/J six-week-old male mice were injected (subcutaneous dorsum) with $1 \times 10^6$ tumor cells. Visible tumors first appeared after 3–4 days. When tumors were approximately 1500 $mm^3$ in size, mice were randomized into two groups. The primary tumor was completely excised in the first group and left intact in the second group after a sham operation. Although tumors from 500 $mm^3$ to 3000 $mm^3$ inhibited growth of metastases, 1500 $mm^3$ was the largest primary tumor that could be safely resected with high survival and no local recurrence.

After 21 days, all mice were sacrificed and autopsied. In mice with an intact primary tumor, there were four +2 visible metastases, compared to fifty +5 metastases in the mice in which the rumor had been removed (p<0.0001). These data were confirmed by lung weight, which correlates closely with tumor burden, as has been previously demonstrated. There was a 400% increase in wet lung weight in the mice that had their tumors removed compared to mice in which the tumor remained intact (p<0.0001).

This experimental model gave reproducible data and the experiment described is reproducible. This tumor is labeled "Lewis lung carcinoma - low metastatic" (LLC-Low). The tumor also suppressed metastases in a nearly identical pattern in SCID mice, which are deficient in both B and T lymphocytes.

EXAMPLE 2

Isolation of a variant of Lewis lung carcinoma tumor that is highly metastatic, whether or not the primary tumor is removed.

A highly metastatic variant of Lewis lung carcinoma arose spontaneously from the LLC-Low cell line in one group of mice and has been isolated according to the methods described in Example I and repeatedly transplanted. This tumor (LLC-High) forms more than 30 visible lung metastases whether or not the primary tumor is present.

EXAMPLE 3

Size of metastases and proliferation rate of tumor cells within them. Effect of the primary tumor that inhibits metastases (LLC-Low).

C57BI6/J mice were used in all experiments. Mice were inoculated subcutaneously with LLC-Low cells, and 14 days later the primary rumor was removed in half of the mice. At 5, 10 and 15 days after the rumor had been removed, mice were sacrificed. Histological sections of lung metastases were obtained. Mice with an intact primary minor had micrometastases in the lung which were not neovascularized. These metastases were restricted to a diameter of 12–15 cell layers and did not show a significant size increase even 15 days after tumor removal. In contrast, animals from which the primary tumor was removed, revealed large vascularized metastases as early as 5 days after operation. These metastases underwent a further 4-fold increase in volume by the 15th day after the tumor was removed (as reflected by lung weight and histology). Approximately 50% of the animals who had a primary tumor removed died of lung metastases before the end of the experiment. All animals with an intact primary rumor survived to the end of the experiment.

Replication rate of tumor cells within metastases was determined by counting nuclei stained with BrdU which had been previously injected into the mice. The high percentage of tumor cells incorporating BrdU in small, avascular metastases of animals with an intact primary tumor was equivalent to the BrdU incorporation of tumor cells in the large vascularized metastases of mice from which the primary tumor had been removed (FIG. 3A). This finding suggests that the presence of a primary tumor has no direct effect on the replication rate of tumor cells within a metastasis.

Figure 3B:
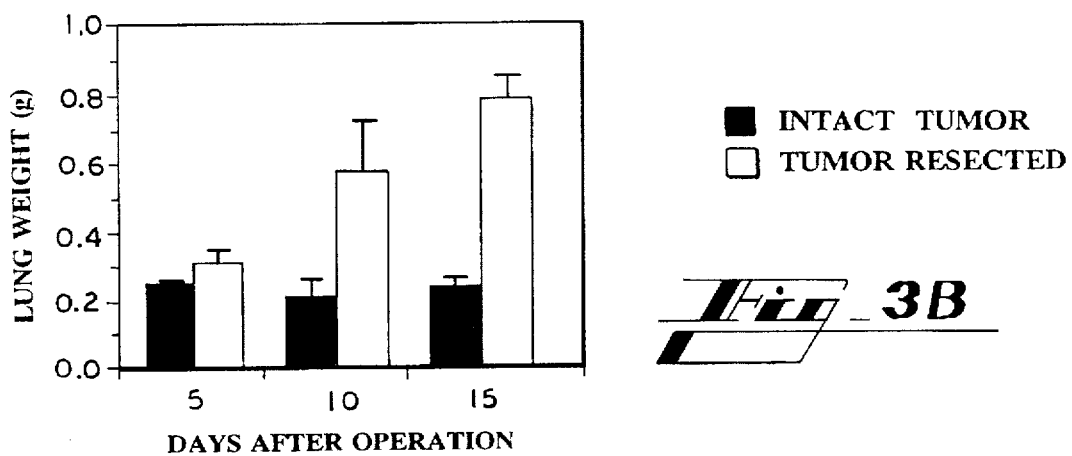
FIG. 3B shows mouse lung weights in the presence or absence of a primary tumor.

FIG. 3A shows BrdU labeling index of tumor cells in the lung in the presence or absence of a primary tumor. Before immunohistochemical staining, sections were permeabilized with 0.2 M HCl for 10 minutes and digested with 1 µg/ml proteinase K (Boehringer Mannheim GmbH, Mannheim, Germany) in 0.2 M Tris-HCl 2 mM $CaCl_2$ at 37° C. for 15 minutes. Labeling index was estimated by counting percentage of positive nuclei at 250 power. FIG. 3B depicts an analysis of total lung weight of tumors with primary tumors intact or removed 5, 10 and 15 days after operation. Animals were sacrificed 6 hours after intraperitoneal injection of BrdU (0.75 mg/mouse).

EXAMPLE 4
Inhibition of angiogenesis in lung metastases in the presence of an intact primary tumor.

To measure the degree of vascularization in lung metastases, tissues were stained with antibodies against von Willebrand factor (an endothelial specific marker, available from Dako Inc., Carpenteria, Calif.). Metastases from animals with intact tumors formed a thin cuff (8–12 tumor cell layers) around existing pulmonary vessels. Except for the endothelial cells of the vessel lining, no or few cells were positive for von Willebrand factor. In contrast, lung metastases of animals 5 days after removal of the primary tumor were not only larger but were also infiltrated with capillary sprouts (arrows) containing endothelial cells which stained strongly for von Willebrand factor.

In immunohistochemical analysis of the presence of endothelial cells in lung metastases, lung metastasis with the primary tumor intact 19 days after inoculation in the lung, had a cuff of tumor cells around a pre-existing microvessel in the lung. The metastasis was limited to 8 to 12 cell layers. There was no evidence of neovascularization around the microvessel, and it did not contain any new microvessels. This was typical of the maximum size of an avascular pre-angiogenic metastasis.

In an immunohistochemical analysis of tissue collected five days after the primary tumor was resected (19 days after inoculation of the primary tumor), the metastasis surrounded a pre-existing vessel in the lung. In contrast, in the sample where the primary tumor was not resected, the tumor was neovascularized. Thus, an intact primary tumor inhibits formation of new capillary blood vessels in metastases, but proliferation of tumor cells within a metastasis are not affected by the primary tumor.

EXAMPLE 5
A primary tumor inhibits angiogenesis of a second tumor implanted in the mouse cornea. Growth of this second tumor is inhibited.

A 0.25 to 0.5 $mm^2$ Lewis lung tumor (LLC-Low) was implanted in the mouse cornea on day 0. (Muthukkaruppan Vr., et al., Angiogenesis in the mouse cornea. *Science* 205:1416–1418, 1979) A primary tumor was formed by inoculating $1 \times 10^6$ LLC-Low cells subcutaneously in the dorsum, either 4 or 7 days before the corneal implant; or on the day of the corneal implant; or 4 or 7 days after the corneal implant. Control mice received the corneal implant but not the subcutaneous tumor. Other control mice received the corneal implant and an inoculation of LLC-High minor cells in the dorsum 4 days before the corneal implant. The corneas were evaluated daily by slit-lamp stereomicroscopy for the growth of the corneal tumor (measured by an ocular micrometer) and for the growth of new capillary vessels from the edge of the corneal limbus.

In control mice not bearing a primary subcutaneous tumor, a majority of corneas (6/8) developed neovascularization starting at day 6 to 7 days after corneal implantation and continuing to day 10. By day 10, the vascularized corneal tumors had reached approximately a quarter of the volume of the whole eye. In the presence of the primary subcutaneous LLC-Low minor, the corneal implants did not become vascularized if the primary was in place by at least 4 days or more before the corneal implant (Table 1). In the absence of neovascularization, corneal tumors grew slowly as thin, white, avascular discs within the cornea.

However, if the primary tumor was not implanted until 4 days after the corneal implant, corneas became vascularized and 3/3 corneal tumors grew at similar rates as the non-tumor bearing controls. In the presence of the primary subcutaneous LLC-High tumor, the majority of corneas (2/3) developed neovascularization starting at day 7 after corneal implantation and continuing to day 10. By day 10, the vascularized corneal tumors again had reached approximately a quarter of the volume of the whole eye.

TABLE 1

Inhibition of tumor angiogenesis in the cornea by a primary subcutaneous tumor. [All primary tumors are LLC-Low except (*) which is LLC-High].

| | | | | | | | |
|---|---|---|---|---|---|---|---|
| Day of eye implant | 0 | 0 | 0 | 0 | 0 | 0 | 0 |
| Day of primary tumor implant | −7 | −4 | −4* | 0 | none | +4 | +7 |
| Number of mice with new corneal vessels at day 10 | 2/10 | 0/9 | 2/3 | 2/3 | 6/8 | 3/3 | 2/3 |

It would be expected that 0/10 corneas would show neovascularization when the primary LLC-Low subcutaneous tumor was implanted 7 days before the eye tumor implant (i.e. −7). However, 2 of the tumors (2/10) had become necrotic because they were too large (>3 $cm^3$).

EXAMPLE 6
Primary intact tumor inhibits angiogenesis induced by a secondary subcutaneous implant of basic fibroblast growth-factor (bFGF).

Although the experiments described in Examples 4 and 5 show that a primary tumor inhibits angiogenesis in a secondary metastasis, these studies do not reveal whether the primary tumor: (i) inhibits endothelial proliferation (or angiogenesis) directly, or (ii) indirectly by down-regulating the angiogenic activity of the metastatic tumor cells. To distinguish between these two possibilities, a focus of subcutaneous angiogenesis was induced by an implant of matrigel containing basic fibroblast growth factor (bFGF). (Passaniti A, et al., A simple, quantitative method for assessing angiogenesis and anti-angiogenic agents using reconstituted basement membrane, heparin and fibroblast growth factor. *Lab. Invest.* 67:519, 1992)

Figure 4:
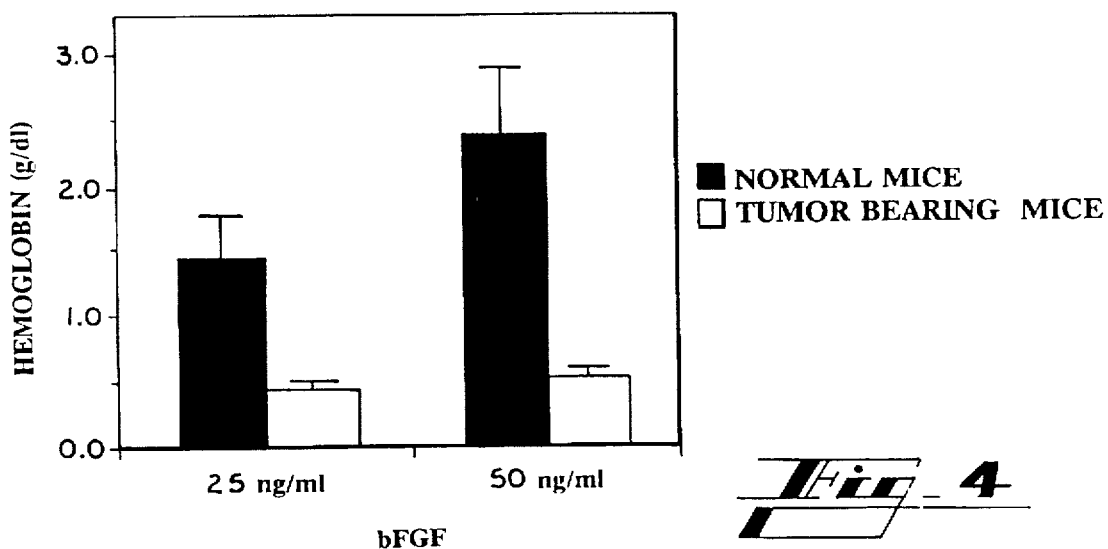
FIG. 4 shows Matrigel analysis of the influence of a Lewis lung primary tumor on bFGF driven angiogenesis in vivo.

Matrigel (an extract of basement membrane proteins), containing either 25 or 50 ng/ml bFGF in the presence of heparin, was injected subcutaneously on the ventral surface of normal and tumor-bearing mice (LLC-Low). Mice were sacrificed 4 days later and hemoglobin concentration in the gel was measured to quantify blood vessel formation. It has previously been shown that the number of new vessels which enter the matrigel is correlated with hemoglobin concentration. (Folkman J., Angiogenesis and its inhibitors in "*Important Advances in Oncology* 1985", V T DeVita, S. Hellman and S. Rosenberg, editors, J. B. Lippincott, Philadelphia 1985) Some gels were also prepared for histological examination. In normal mice, matrigel pellets which contained 50 ng/ml bFGF were completely red. They were heavily invaded by new capillary vessels, and contained 2.4 g/dl hemoglobin. Matrigel which lacked bFGF was translucent and gray and contained only 0.4 g/dl hemoglobin (a 6-fold difference). In contrast, matrigel from mice with a primary tumor contained only 0.5 g/dl (FIG. 4).

The near complete inhibition of angiogenesis in this experiment suggests that the presence of a Lewis lung primary tumor can inhibit bFGF-induced angiogenesis directly.

EXAMPLE 7

Transfer of serum from a tumor-bearing animal to an animal from which the primary tumor has been removed suppresses metastases.

Mice were implanted with Lewis lung carcinoma as described above. After 15 days, when tumors were approximately 1500 mm$^3$, the mice were randomized into four groups. Three groups underwent complete surgical resection of the primary tumor; in one group the tumors were left in place (after a sham surgical procedure). The mice in the three resection groups then received daily intraperitoneal injections of saline, serum from normal nontumor bearing mice, or serum from mice with 1500 mm$^3$ Lewis lung carcinomas. The group of mice with the tumors left intact received intraperitoneal saline injections. All mice were treated for 21 days, after which the animals were euthanized and lung metastases were counted (Table 2).

TABLE 2

| Treatment (Intraperitoneal Injections) | Primary Tumor Removed | | | Primary |
|---|---|---|---|---|
| | Saline | Serum from normal mice | Serum from tumor-bearing mice | Tumor Intact Saline Injections |
| Number of Lung Metastases: | 55 ± 5 | 50 ± 4 | 7 ± 2 | 3 ± 1 |

These results were confirmed by lung weight. p=<0.0001 for the difference between the two groups [(55 & 50) vs. (7 & 3)].

EXAMPLE 8

Bovine capillary endothelial (BCE) cell assay

BCE cells are used between passages 9 and 14 only. At day 0, BCE cells are plated onto gelatinized (1.5% gelatin in PBS at 37°, 10% $CO_2$ for 24 hours and then rinsed with 0.5 ml PBS) 24 well plates at a concentration of 12,500 cells/well. Cell counts are performed using a hemocytometer. Cells are plated in 500 µl DMEM with 10% heat-inactivated (56° C. for 20 minutes) bovine calf serum and 1% glutamine-pen-strep (GPS).

BCE cells are challenged as follows: Media is removed and replaced with 250 µl of DMEM/5% BCS/1% GPS. The sample to be tested is then added to wells. (The amount varies depending on the sample being tested) Plates are placed at 37° C./10% $CO_2$ for approximately 10 minutes. 250 µl of DMEM/5% BCS/1% GPS with 2 ng/ml bFGF is added to each well. The final media is 500 µl of DMEM/5% BCS/1% GPS/with 1 ng/ml bFGF. The plate is returned to 37° C./10% $CO_2$ incubator for 72 hours.

At day 4, cells are counted by removing the medium and then trypsinizing all wells (0.5 ml trypsin/EDTA) for 2 to 3 minutes. The suspended cells are then transferred to scintillation vials with 9.5 ml Hemetall and counted using a Coulter counter. A unit of activity is that mount of serum containing angiostatin that is capable of producing half-maximal inhibition of capillary endothelial proliferation when endothelial cells are incubated in bFGF 1 ng/ml for 72 hours.

EXAMPLE 9

Serum from mice bearing the low metastatic Lewis lung tumor (LLC-Low) inhibits capillary endothelial cell proliferation in vitro.

Bovine capillary endothelial cells were stimulated by basic fibroblast growth factor (bFGF 1 ng/ml), in a 72-hour proliferation assay. The serum of tumor-bearing mice added to these cultures inhibited endothelial cell proliferation in a dose-dependent and reversible manner. Normal serum was not inhibitory (FIG. 5). Endothelial cell proliferation was inhibited in a similar manner (relative to controls) by serum obtained from rumor-bearing nu/nu mice and SCID mice. After the primary minor was removed, angiostatin activity disappeared from the serum by 3–5 days.

Tumor-bearing serum also inhibited bovine aortic endothelial cells and endothelial cells derived from a spontaneous mouse hemangioendothelioma, (Obeso, et al., "Methods in Laboratory Investigation. A Hemangioendothelioma-derived cell line; Its use as a Model for the Study of Endothelial Cell Biology," *Lab Invest.*, 63(2), pgs 259–269, 1990) but did not inhibit Lewis lung tumor cells, 3T3 fibroblasts, aortic smooth muscle cells, mink lung epithelium, or W138 human fetal lung fibroblasts.

EXAMPLE 10

Serum from mice bearing the Lewis lung tumor (LLC-High) that does not inhibit metastases, does not inhibit capillary endothelial cell proliferation in vitro.

Serum from mice bearing a primary tumor of the LLC-High did not significantly inhibit proliferation of bFGF-stimulated bovine capillary endothelial cells relative to controls. Also, when this serum was subjected to the first two steps of purification (heparin-Sepharose chromatography and gel filtration), angiostatin activity was not found in any fractions.

EXAMPLE 11

Ascites from Lewis lung carcinoma (low metastatic), also generates angiostatin in serum.

Mice received intraperitoneal injections of either LLC-Low or LLC-High tumor cells (10$^6$), and one week later, 1–2 ml of bloody ascites was obtained from each of 10–20 mice. Mesenteric tumor seeding was seen. The mice were then euthanized. Serum was obtained by cardiac puncture. Serum was also obtained from normal, non-tumor-bearing mice as a control. Serum and ascites were centrifuged to remove cells, and the supernate was assayed on bovine capillary endothelial cells stimulated by bFGF (1 ng/ml) (see Example 8). Ascites originating from both tumor types stimulated significant proliferation of capillary endothelial cells (e.g., 100% proliferation) over controls after 72 hours (FIG. 6A and 6B). In contrast, serum from the low metastatic mice inhibited endothelial cell proliferation (FIG. 6A). The serum from the high metastatic line was stimulatory by 200% (FIG. 6B).

These data show that the ascites of the low metastatic line contains a predominance of endothelial growth stimulator over angiostatin. This condition is analogous to a solid primary tumor. Furthermore, angiostatin activity appears in the serum, as though it were unopposed by stimulatory activity. This pattern is similar to the solid primary tumor (LLC-Low). The ascites from the high metastatic tumor (LLC-High) also appears to contain a predominance of endothelial cell stimulator, but angiostatin cannot be identified in the serum.

EXAMPLE 12

Fractionation of angiostatin from serum by column chromatography and analysis of growth-inhibitory fractions by SDS-PAGE.

To purify the angiostatin(s), serum was pooled from tumor-bearing mice. The inhibitory activity, assayed according the above-described in vitro inhibitor activity assay, was sequentially chromatographed using heparin-Sepharose, Biogel AO.5m agarose, and several cycles of C4-reverse phase high performance liquid chromatography (HPLC). SDS-PAGE of the HPLC fraction which contained endothelial inhibitory activity, revealed a discrete band of apparent reduced $M_r$ of 38,000 Daltons, which was purified approximately 1 million-fold (see Table 3) to a specific activity of approximately $2 \times 10^7$. At different stages of the purification, pooled fractions were tested with specific antibodies for the presence of known endothelial inhibitors. Platelet factor-4, thrombospondin, or transforming growth factor beta, were not found in the partially purified or purified fractions.

TABLE 3

|  | Specific activity (units*/mg) | Fold purification |
|---|---|---|
| Serum | 1.69 | 1 |
| Heparin Sepharose | 14.92 | 8.8 |
| Bio-gel AO.5m | 69.96 | 41.4 |
| HPLC/C4 | $2 \times 10^7$ | $1.2 \times 10^6$ |

*A unit of activity is that amount of serum containing angiostatin that is capable of producing half-maximal inhibition of capillary endothelial proliferation when endothelial cells are incubated in bFGF 1 ng/ml for 72 hours.

EXAMPLE 13

Fractionation of angiostatin from urine by column chromatography and analysis of growth-inhibitory fractions by SDS-PAGE.

Purification of the endothelial cell inhibitor(s) from serum is hampered by the small volume of serum that can be obtained from each mouse and by the large amount of protein in the serum.

Urine from tumor bearing mice was analyzed and found that it contains an inhibitor of endothelial cell proliferation that is absent from the urine of non-tumor bearing mice and from mice with LLC-high tumors. Purification of the endothelial cell inhibitory activity was carded out by the same strategy that was employed for purification of serum (described above).

FIGS. 7A and 7B shows C4 reverse phase chromatography of partially purified serum or urine from tumor-bearing animals. All fractions were assayed on bovine capillary endothelial cells with bFGF in a 72-hour proliferation assay as described in Example 8. A discrete peak of inhibition was seen in both cases eluting at 30–35% acetonitrile in fraction 23.

SDS-poly acrylamide gel electrophoresis of inhibitory fraction from third cycle of C4 reverse phase chromatography of serum from tumor-bearing animals showed a single band at about 38,000 Daltons.

EXAMPLE 14

Characterization of circulating angiostatin.

Endothelial inhibition was assayed according to the procedure described in Example 9. Angiostatin was isolated on a Synchropak HPLC C4 column. (Synchrom, Inc. Lafayette, Ind.) The inhibitor was eluted at 30 to 35% acetonitrile gradient. On a sodium dodecyl sulfate polyacrylamide gel electrophoresis (PAGE) gel under reducing conditions (β-mercaptoethanol(5% v/v), the protein band with activity eluted at 38 kilodaltons. Under non-reducing conditions, the protein with activity eluted at 28 kilodaltons. The activity is found at similar points whether the initial sample was isolated from urine or from serum. Activity was not detected with any other bands.

Activity associated with the bands was lost when heated (100° C. for 10 minutes) or treated with trypsin. When the band with activity was extracted with a water/chloroform mixture (1:1), the activity was found in the aqueous phase only.

EXAMPLE 15

Purification of inhibitory fragments from human plasminogen:

Plasminogen lysine binding site I was obtained from Sigma Chemical Company. The preparation is purified human plasminogen after digestion with elastase. Lysine binding site I obtained in this manner is a population of peptides that contain, in aggregate, at least the first three triple-loop structures (numbers 1 through 3) in the plasmin A-chain (Kringle 1+2+3). (Sottrup-Jensen, L., et al. in *Progress in Chemical Fibrinolysis and Thrombolysis*, Vol. 3, 191, Davidson, J. F., et al. eds. Raven Press, New York 1978 and Wiman, B., et al., *Biochemica et Biophysica Acta*, 579, 142 (1979)). Plasminogen lysine binding site I (Sigma Chemical Company, St. Louis, Mo.) was resuspended in water and applied to a C4-reversed phase column that had been equilibrated with HPLC-grade water/0.1% TFA. The column was eluted with a gradient of water/0.1% TFA to acetonitrile/0.1% TFA and fractions were collected into polypropylene tubes. An aliquot of each was evaporated in a speed vac, resuspended with water, and applied to BCE's in a proliferation assay. This procedure was repeated two times for the inhibitory fractions using a similar gradient for elution. The inhibitory activity eluted at 30–35% acetonitrile in the final run of the C4 column. SDS-PAGE of the inhibitory fraction revealed 3 discreet bands of apparent reduced molecular mass of 40, 42.5, and 45 kd. SDS-PAGE under non-reducing conditions revealed three bands of molecular mass 30, 32.5, and 35 kd respectively.

EXAMPLE 16

Extraction of inhibitory activity from SDS-PAGE

Purified inhibitory fractions from human plasminogen based purifications were resolved by SDS-PAGE under non-denaturing conditions. Areas of the gel corresponding to bands seen in neighboring lanes loaded with the same samples by silver staining were cut from the gel and incubated in one ml of phosphate buffered saline at 4° C. for 12 hours in polypropylene tubes. The supernatant was removed and dialyzed twice against saline for 6 hours (MWCO= 6–8000) and twice against distilled water for 6 hours. The dialysate was evaporated by vacuum centrifugation. The product was resuspended in saline and applied to bovine capillary endothelial cells stimulated by 1 ng/ml basic fibroblast growth factor in a 72 hour assay. Protein extracted from each of the three bands inhibited the capillary endothelial cells.

EXAMPLE 17

Plasminogen Fragment Treatment Studies

Mice were implanted with Lewis lung carcinomas and under went resections when the tumors were 1500–2000 mm$^3$. On the day of operation, mice were randomized into 6 groups of 6 mice each. The mice received daily intraperitoneal injections with the three purified inhibitory fragments of human plasminogen, whole human plasminogen, urine from tumor-bearing animals, urine from normal mice, or saline. One group of tumor-bearing animals that had only a sham procedure was treated with saline injections. Immediately after removal of the primary tumor, the mice receive an intraperitoneal injection of 24 µg (1.2 mg/kg/day/mouse) of the inhibitory plasminogen fragments as a loading dose. They then receive a daily intraperitoneal injections of 12 µg of the inhibitory fragment (0.6 mg/kg/day/mouse) for the duration of the experiment. Control mice receive the same dose of the whole plasminogen molecule after tumor removal. For the urine treatments, the urine of normal or tumor bearing mice is filtered, dialyzed extensively, lyophilized, and then resuspended in sterile water to obtain a 250 fold concentration. The mice are given 0.8 ml of the dialyzed urine concentrate, either from tumor bearing mice or normal mice, in two intraperitoneal injections on the day of removal of the primary tumor as a loading dose. They then receive daily intraperitoneal injections of 0.4 ml of the dialyzed and concentrated urine for the course of the experiment. Treatments were continued for 13 days at which point all mice were sacrificed and autopsied.

The results of the experiment are shown in FIGS. 8 and 9. FIG. 8 shows surface lung metastases after the 13 day treatment. Surface lung metastases refers to the number of metastases seen in the lungs of the mice at autopsy. A stereomicroscope was used to count the metastases. FIG. 8 shows the mean number of surface lung metastases that was counted and the standard error of the mean. As shown, the group of mice with the primary tumor present showed no metastases. The mice in which the primary tumor was resected and were treated with saline showed extensive metastases. The mice treated with the human derived plasminogen fragment showed no metastases. The mice treated with whole plasminogen showed extensive metastases indicating that the whole plasminogen molecule has no endothelial inhibitory activity. Those mice treated dialyzed and concentrated urine from tumor bearing mice showed no metastases. Mice treated with concentrated urine from normal mice showed extensive metastases. When the weight of the lung was measured, similar results were obtained (FIG. 9)

EXAMPLE 18

Amino acid sequence of murine and human angiostatin.

The amino acid sequence of angiostatin isolated from mouse urine and angiostatin isolated from the human lysine binding site I fragment preparation was determined on an Applied Biosystem Model 477A protein sequencer. Phenylthiohydantoin amino acid fractions were identified with an on-line ABI Model 120A HPLC. The amino acid sequence determined from the N-terminal sequence and the tryptic digests of the murine and human angiostatin indicate that the sequence of the angiostatin is similar to the sequence beginning at amino acid number 98 of murine plasminogen. Thus, the amino acid sequence of the angiostatin is a molecule comprising a protein having a molecular weight of between approximately 38 kilodaltons and 45 kilodaltons as determined by reducing polyacrylamide gel electrophoresis and having an amino acid sequence substantially similar to that of a murine plasminogen fragment beginning at amino acid number 98 of an intact murine plasminogen molecule. The beginning amino acid sequence of the murine angiostatin (SEQ ID NO: 2) is shown in FIGS. 1A and 1B. The length of the amino acid sequence, may be slightly longer or shorter than that shown in the FIGS. 1A and 1B.

N terminal amino acid analysis and tryptic digests of the active fraction of human lysine binding site I (See Example 15) show that the sequence of the fraction begins at approximately amino acid 97 or 99 of human plasminogen and the human angiostatin is homologous with the murine angiostatin. The beginning amino acid sequence of the human angiostatin (starting at amino acid 98) is shown in FIGS. 2A, 2B and 2C, (SEQ ID NO: 3). The amino acid sequence of murine and human angiostatin is compared in FIGS. 2A, 2B and 2C to corresponding internal amino acid sequences from plasminogen of other species including porcine, bovine, and Rhesus monkey plasminogen, indicating the presence of angiostatin in those species.

It should be understood, of course, that the foregoing relates only to preferred embodiments of the present invention and that numerous modifications or alterations may be made therein without departing from the spirit and the scope of the invention as set forth in the appended claims.

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 812
        ( B ) TYPE: amino acid
        ( D ) TOPOLOGY: linear ( x i ) SEQUENCE DESCRIPTION: SEQ ID NO: 1:

Met Asp His Lys Glu Val Ile Leu Leu Phe Leu Leu Leu Leu Lys

| 1 | | | | 5 | | | | | 10 | | | | | 15 |
|---|---|---|---|---|---|---|---|---|---|---|---|---|---|---|
| Pro | Gly | Gln | Gly | Asp | Ser | Leu | Asp | Gly | Tyr | Ile | Ser | Thr | Gln | Gly |
| | | | | 20 | | | | | 25 | | | | | 30 |
| Ala | Ser | Leu | Phe | Ser | Leu | Thr | Lys | Lys | Gln | Leu | Ala | Ala | Gly | Gly |
| | | | | 35 | | | | | 40 | | | | | 45 |
| Val | Ser | Asp | Cys | Leu | Ala | Lys | Cys | Glu | Gly | Glu | Thr | Asp | Phe | Val |
| | | | | 50 | | | | | 55 | | | | | 60 |
| Cys | Arg | Ser | Phe | Gln | Tyr | His | Ser | Lys | Glu | Gln | Gln | Cys | Val | Ile |
| | | | | 65 | | | | | 70 | | | | | 75 |
| Met | Ala | Glu | Asn | Ser | Lys | Thr | Ser | Ser | Ile | Ile | Arg | Met | Arg | Asp |
| | | | | 80 | | | | | 85 | | | | | 90 |
| Val | Ile | Leu | Phe | Glu | Lys | Arg | Val | Tyr | Leu | Ser | Glu | Cys | Lys | Thr |
| | | | | 95 | | | | | 100 | | | | | 105 |
| Gly | Ile | Gly | Asn | Gly | Tyr | Arg | Gly | Thr | Met | Ser | Arg | Thr | Lys | Ser |
| | | | | 110 | | | | | 115 | | | | | 120 |
| Gly | Val | Ala | Cys | Gln | Lys | Trp | Gly | Ala | Thr | Phe | Pro | His | Val | Pro |
| | | | | 125 | | | | | 130 | | | | | 135 |
| Asn | Tyr | Ser | Pro | Ser | Thr | His | Pro | Asn | Glu | Gly | Leu | Glu | Glu | Asn |
| | | | | 140 | | | | | 145 | | | | | 150 |
| Tyr | Cys | Arg | Asn | Pro | Asp | Asn | Asp | Glu | Gln | Gly | Pro | Trp | Cys | Tyr |
| | | | | 155 | | | | | 160 | | | | | 165 |
| Thr | Thr | Asp | Pro | Asp | Lys | Arg | Tyr | Asp | Tyr | Cys | Asn | Ile | Pro | Glu |
| | | | | 170 | | | | | 175 | | | | | 180 |
| Cys | Glu | Glu | Glu | Cys | Met | Tyr | Cys | Ser | Gly | Glu | Lys | Tyr | Glu | Gly |
| | | | | 185 | | | | | 190 | | | | | 195 |
| Lys | Ile | Ser | Lys | Thr | Met | Ser | Gly | Leu | Asp | Cys | Gln | Ala | Trp | Asp |
| | | | | 200 | | | | | 205 | | | | | 210 |
| Ser | Gln | Ser | Pro | His | Ala | His | Gly | Tyr | Ile | Pro | Ala | Lys | Phe | Pro |
| | | | | 215 | | | | | 220 | | | | | 225 |
| Ser | Lys | Asn | Leu | Lys | Met | Asn | Tyr | Cys | His | Asn | Pro | Asp | Gly | Glu |
| | | | | 230 | | | | | 235 | | | | | 240 |
| Pro | Arg | Pro | Trp | Cys | Phe | Thr | Thr | Asp | Pro | Thr | Lys | Arg | Trp | Glu |
| | | | | 245 | | | | | 250 | | | | | 255 |
| Tyr | Cys | Asp | Ile | Pro | Arg | Cys | Thr | Thr | Pro | Pro | Pro | Pro | Pro | Ser |
| | | | | 260 | | | | | 265 | | | | | 270 |
| Pro | Thr | Tyr | Gln | Cys | Leu | Lys | Gly | Arg | Gly | Glu | Asn | Tyr | Arg | Gly |
| | | | | 275 | | | | | 280 | | | | | 285 |
| Thr | Val | Ser | Val | Thr | Val | Ser | Gly | Lys | Thr | Cys | Gln | Arg | Trp | Ser |
| | | | | 290 | | | | | 295 | | | | | 300 |
| Glu | Gln | Thr | Pro | His | Arg | His | Asn | Arg | Thr | Pro | Glu | Asn | Phe | Pro |
| | | | | 305 | | | | | 310 | | | | | 315 |
| Cys | Lys | Asn | Leu | Glu | Glu | Asn | Tyr | Cys | Arg | Asn | Pro | Asp | Gly | Glu |
| | | | | 320 | | | | | 325 | | | | | 330 |
| Thr | Ala | Pro | Trp | Cys | Tyr | Thr | Thr | Asp | Ser | Gln | Leu | Arg | Trp | Glu |
| | | | | 335 | | | | | 340 | | | | | 345 |
| Tyr | Cys | Glu | Ile | Pro | Ser | Cys | Glu | Ser | Ser | Ala | Ser | Pro | Asp | Gln |
| | | | | 350 | | | | | 355 | | | | | 360 |
| Ser | Asp | Ser | Ser | Val | Pro | Pro | Glu | Glu | Gln | Thr | Pro | Val | Val | Gln |
| | | | | 365 | | | | | 370 | | | | | 375 |
| Glu | Cys | Tyr | Gln | Ser | Asp | Gly | Gln | Ser | Tyr | Arg | Gly | Thr | Ser | Ser |
| | | | | 380 | | | | | 385 | | | | | 390 |
| Thr | Thr | Ile | Thr | Gly | Lys | Lys | Cys | Gln | Ser | Trp | Ala | Ala | Met | Phe |
| | | | | 395 | | | | | 400 | | | | | 405 |

-continued

```
Pro His Arg His Ser Lys Thr Pro Glu Asn Phe Pro Asp Ala Gly
            410             415             420

Leu Glu Met Asn Tyr Cys Arg Asn Pro Asp Gly Asp Lys Gly Pro
            425             430             435

Trp Cys Tyr Thr Thr Asp Pro Ser Val Arg Trp Glu Tyr Cys Asn
            440             445             450

Leu Lys Arg Cys Ser Glu Thr Gly Gly Ser Val Val Glu Leu Pro
            455             460             465

Thr Val Ser Gln Glu Pro Ser Gly Pro Ser Asp Ser Glu Thr Asp
            470             475             480

Cys Met Tyr Gly Asn Gly Lys Asp Tyr Arg Gly Lys Thr Ala Val
            485             490             495

Thr Ala Ala Gly Thr Pro Cys Gln Gly Trp Ala Ala Gln Glu Pro
            500             505             510

His Arg His Ser Ile Phe Thr Pro Gln Thr Asn Pro Arg Ala Asp
            515             520             525

Leu Glu Lys Asn Tyr Cys Arg Asn Pro Asp Gly Asp Val Asn Gly
            530             535             540

Pro Trp Cys Tyr Thr Thr Asn Pro Arg Lys Leu Tyr Asp Tyr Cys
            545             550             555

Asp Ile Pro Leu Cys Ala Ser Ala Ser Ser Phe Glu Cys Gly Lys
            560             565             570

Pro Gln Val Glu Pro Lys Lys Cys Pro Gly Arg Val Val Gly Gly
            575             580             585

Cys Val Ala Asn Pro His Ser Trp Pro Trp Gln Ile Ser Leu Arg
            590             595             600

Thr Arg Phe Thr Gly Gln His Phe Cys Gly Gly Thr Leu Ile Ala
            605             610             615

Pro Glu Trp Val Leu Thr Ala Ala His Cys Leu Glu Lys Ser Ser
            620             625             630

Arg Pro Glu Phe Tyr Lys Val Ile Leu Gly Ala His Glu Glu Tyr
            635             640             645

Ile Arg Gly Leu Asp Val Gln Glu Ile Ser Val Ala Lys Leu Ile
            650             655             660

Leu Glu Pro Asn Asn Arg Asp Ile Ala Leu Leu Lys Leu Ser Arg
            665             670             675

Pro Ala Thr Ile Thr Asp Lys Val Ile Pro Ala Cys Leu Pro Ser
            680             685             690

Pro Asn Tyr Met Val Ala Asp Arg Thr Ile Cys Tyr Ile Thr Gly
            695             700             705

Trp Gly Glu Thr Gln Gly Thr Phe Gly Ala Gly Arg Leu Lys Glu
            710             715             720

Ala Gln Leu Pro Val Ile Glu Asn Lys Val Cys Asn Arg Val Glu
            725             730             735

Tyr Leu Asn Asn Arg Val Lys Ser Thr Glu Leu Cys Ala Gly Gln
            740             745             750

Leu Ala Gly Gly Val Asp Ser Cys Gln Gly Asp Ser Gly Gly Pro
            755             760             765

Leu Val Cys Phe Glu Lys Asp Lys Tyr Ile Leu Gln Gly Val Thr
            770             775             780

Ser Trp Gly Leu Gly Cys Ala Arg Pro Asn Lys Pro Gly Val Tyr
            785             790             795

Val Arg Val Ser Arg Phe Val Asp Trp Ile Glu Arg Glu Met Arg
            800             805             810
```

Asn Asn
   812

(2) INFORMATION FOR SEQ ID NO: 2:

(i) SEQUENCE CHARACTERISTICS:
      (A) LENGTH: 339
      (B) TYPE: amino acid
      (D) TOPOLOGY: linear (xi) SEQUENCE DESCRIPTION: SEQ ID NO: 2:

```
Val  Tyr  Leu  Ser  Glu  Cys  Lys  Thr  Gly  Ile  Gly  Asn  Gly  Tyr  Arg
 1                   5                   10                           15

Gly  Thr  Met  Ser  Arg  Thr  Lys  Ser  Gly  Val  Ala  Cys  Gln  Lys  Trp
                    20                   25                           30

Gly  Ala  Thr  Phe  Pro  His  Val  Pro  Asn  Tyr  Ser  Pro  Ser  Thr  His
                    35                   40                           45

Pro  Asn  Glu  Gly  Leu  Glu  Glu  Asn  Tyr  Cys  Arg  Asn  Pro  Asp  Asn
                    50                   55                           60

Asp  Glu  Gln  Gly  Pro  Trp  Cys  Tyr  Thr  Thr  Asp  Pro  Asp  Lys  Arg
                    65                   70                           75

Tyr  Asp  Tyr  Cys  Asn  Ile  Pro  Glu  Cys  Glu  Glu  Cys  Met  Tyr
                    80                   85                           90

Cys  Ser  Gly  Glu  Lys  Tyr  Glu  Gly  Lys  Ile  Ser  Lys  Thr  Met  Ser
                    95                  100                          105

Gly  Leu  Asp  Cys  Gln  Ala  Trp  Asp  Ser  Gln  Ser  Pro  His  Ala  His
                   110                  115                          120

Gly  Tyr  Ile  Pro  Ala  Lys  Phe  Pro  Ser  Lys  Asn  Leu  Lys  Met  Asn
                   125                  130                          135

Tyr  Cys  His  Asn  Pro  Asp  Gly  Glu  Pro  Arg  Pro  Trp  Cys  Phe  Thr
                   140                  145                          150

Thr  Asp  Pro  Thr  Lys  Arg  Trp  Glu  Tyr  Cys  Asp  Ile  Pro  Arg  Cys
                   155                  160                          165

Thr  Thr  Pro  Pro  Pro  Pro  Pro  Ser  Pro  Thr  Tyr  Gln  Cys  Leu  Lys
                   170                  175                          180

Gly  Arg  Gly  Glu  Asn  Tyr  Arg  Gly  Thr  Val  Ser  Val  Thr  Val  Ser
                   185                  190                          195

Gly  Lys  Thr  Cys  Gln  Arg  Trp  Ser  Glu  Gln  Thr  Pro  His  Arg  His
                   200                  205                          210

Asn  Arg  Thr  Pro  Glu  Asn  Phe  Pro  Cys  Lys  Asn  Leu  Glu  Glu  Asn
                   215                  220                          225

Tyr  Cys  Arg  Asn  Pro  Asp  Gly  Glu  Thr  Ala  Pro  Trp  Cys  Tyr  Thr
                   230                  235                          240

Thr  Asp  Ser  Gln  Leu  Arg  Trp  Glu  Tyr  Cys  Glu  Ile  Pro  Ser  Cys
                   245                  250                          255

Glu  Ser  Ser  Ala  Ser  Pro  Asp  Gln  Ser  Asp  Ser  Ser  Val  Pro  Pro
                   260                  265                          270

Glu  Glu  Gln  Thr  Pro  Val  Val  Gln  Glu  Cys  Tyr  Gln  Ser  Asp  Gly
                   275                  280                          285

Gln  Ser  Tyr  Arg  Gly  Thr  Ser  Ser  Thr  Ile  Thr  Gly  Lys  Lys
                   290                  295                          300

Cys  Gln  Ser  Trp  Ala  Ala  Met  Phe  Pro  His  Arg  His  Ser  Lys  Thr
                   305                  310                          315

Pro  Glu  Asn  Phe  Pro  Asp  Ala  Gly  Leu  Glu  Met  Asn  Tyr  Cys  Arg
                   320                  325                          330
```

Asn Pro Asp Gly Asp Lys Gly Pro Trp
            335                 339

(2) INFORMATION FOR SEQ ID NO: 3:

(i) SEQUENCE CHARACTERISTICS:
        (A) LENGTH: 339
        (B) TYPE: amino acid
        (D) TOPOLOGY: linear (xi) SEQUENCE DESCRIPTION: SEQ ID NO: 3:

```
Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp
                20                  25                  30

Ser Ser Thr Ser Pro His Arg Pro Arg Phe Ser Pro Ala Thr His
                35                  40                  45

Pro Ser Glu Gly Leu Glu Glu Asn Tyr Cys Arg Asn Pro Asp Asn
                50                  55                  60

Asp Pro Gln Gly Pro Trp Cys Tyr Thr Thr Asp Pro Glu Lys Arg
                65                  70                  75

Tyr Asp Tyr Cys Asp Ile Leu Glu Cys Glu Glu Cys Met His
                80                  85                  90

Cys Ser Gly Glu Asn Tyr Asp Gly Lys Ile Ser Lys Thr Met Ser
                95                  100                 105

Gly Leu Glu Cys Gln Ala Trp Asp Ser Gln Ser Pro His Ala His
                110                 115                 120

Gly Tyr Ile Pro Ser Lys Phe Pro Asn Lys Asn Leu Lys Lys Asn
                125                 130                 135

Tyr Cys Arg Asn Pro Asp Arg Glu Leu Arg Pro Trp Cys Phe Thr
                140                 145                 150

Thr Asp Pro Asn Lys Arg Trp Glu Leu Cys Asp Ile Pro Arg Cys
                155                 160                 165

Thr Thr Pro Pro Pro Ser Ser Gly Pro Thr Tyr Gln Cys Leu Lys
                170                 175                 180

Gly Thr Gly Glu Asn Tyr Arg Gly Asn Val Ala Val Thr Val Ser
                185                 190                 195

Gly His Thr Cys Gln His Trp Ser Ala Gln Thr Pro His Thr His
                200                 205                 210

Asn Arg Thr Pro Glu Asn Phe Pro Cys Lys Asn Leu Asp Glu Asn
                215                 220                 225

Tyr Cys Arg Asn Pro Asp Gly Lys Arg Ala Pro Trp Cys His Thr
                230                 235                 240

Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro
                260                 265                 270

Pro Glu Leu Thr Pro Val Val Gln Asp Cys Tyr His Gly Asp Gly
                275                 280                 285

Gln Ser Tyr Arg Gly Thr Ser Ser Thr Thr Thr Thr Gly Lys Lys
                290                 295                 300

Cys Gln Ser Trp Ser Ser Met Thr Pro His Arg His Gln Lys Thr
                305                 310                 315

Pro Glu Asn Tyr Pro Asn Ala Gly Leu Thr Met Asn Tyr Cys Arg
                320                 325                 330

Asn Pro Asp Ala Asp Lys Gly Pro Trp
```

( 2 ) INFORMATION FOR SEQ ID NO: 4:

( i ) SEQUENCE CHARACTERISTICS:
        ( A ) LENGTH: 339
        ( B ) TYPE: amino acid
        ( D ) TOPOLOGY: linear ( x i ) SEQUENCE DESCRIPTION: SEQ ID NO: 4:

```
Val Tyr Leu Ser Glu Cys Lys Thr Gly Asn Gly Lys Asn Tyr Arg
 1               5                  10                  15
Gly Thr Met Ser Lys Thr Arg Thr Gly Ile Thr Cys Gln Lys Trp
                20                  25                  30
Ser Ser Thr Ser Pro His Arg Pro Thr Phe Ser Pro Ala Thr His
                35                  40                  45
Pro Ser Glu Gly Leu Glu Glu Asn Tyr Cys Arg Asn Pro Asp Asn
                50                  55                  60
Asp Gly Gln Gly Pro Trp Cys Tyr Thr Thr Asp Pro Glu Glu Arg
                65                  70                  75
Phe Asp Tyr Cys Asp Ile Pro Glu Cys Glu Asp Glu Cys Met His
                80                  85                  90
Cys Ser Gly Glu Asn Tyr Asp Gly Lys Ile Ser Lys Thr Met Ser
                95                 100                 105
Gly Leu Glu Cys Gln Ala Trp Asp Ser Gln Ser Pro His Ala His
               110                 115                 120
Gly Tyr Ile Pro Ser Lys Phe Pro Asn Lys Asn Leu Lys Lys Asn
               125                 130                 135
Tyr Cys Arg Asn Pro Asp Gly Glu Pro Arg Pro Trp Cys Phe Thr
               140                 145                 150
Thr Asp Pro Asn Lys Arg Trp Glu Leu Cys Asp Ile Pro Arg Cys
               155                 160                 165
Thr Thr Pro Pro Pro Ser Ser Gly Pro Thr Tyr Gln Cys Leu Lys
               170                 175                 180
Gly Thr Gly Glu Asn Tyr Arg Gly Asp Val Ala Val Thr Val Ser
               185                 190                 195
Gly His Thr Cys His Gly Trp Ser Ala Gln Thr Pro His Thr His
               200                 205                 210
Asn Arg Thr Pro Glu Asn Phe Pro Cys Lys Asn Leu Asp Glu Asn
               215                 220                 225
Tyr Cys Arg Asn Pro Asp Gly Glu Lys Ala Pro Trp Cys Tyr Thr
               230                 235                 240
Thr Asn Ser Gln Val Arg Trp Glu Tyr Cys Lys Ile Pro Ser Cys
               245                 250                 255
Glu Ser Ser Pro Val Ser Thr Glu Pro Leu Asp Pro Thr Ala Pro
               260                 265                 270
Pro Glu Leu Thr Pro Val Val Gln Glu Cys Tyr His Gly Asp Gly
               275                 280                 285
Gln Ser Tyr Arg Gly Thr Ser Ser Thr Thr Thr Thr Gly Lys Lys
               290                 295                 300
Cys Gln Ser Trp Ser Ser Met Thr Pro His Trp His Glu Lys Thr
               305                 310                 315
Pro Glu Asn Phe Pro Asn Ala Gly Leu Thr Met Asn Tyr Cys Arg
               320                 325                 330
Asn Pro Asp Ala Asp Lys Gly Pro Trp
               335                 339
```

( 2 ) INFORMATION FOR SEQ ID NO: 5:

( i ) SEQUENCE CHARACTERISTICS:
        ( A ) LENGTH: 339
        ( B ) TYPE: amino acid
        ( D ) TOPOLOGY: linear ( x i ) SEQUENCE DESCRIPTION: SEQ ID NO: 5:

```
Ile Tyr Leu Ser Glu Cys Lys Thr Gly Asn Gly Lys Asn Tyr Arg
 1               5                  10                  15
Gly Thr Thr Ser Lys Thr Lys Ser Gly Val Ile Cys Gln Lys Trp
                20                  25                  30
Ser Val Ser Ser Pro His Ile Pro Lys Tyr Ser Pro Glu Lys Phe
                35                  40                  45
Pro Leu Ala Gly Leu Glu Glu Asn Tyr Cys Arg Asn Pro Asp Asn
                50                  55                  60
Asp Glu Lys Gly Pro Trp Cys Tyr Thr Thr Asp Pro Glu Thr Arg
                65                  70                  75
Phe Asp Tyr Cys Asp Ile Pro Glu Cys Glu Asp Glu Cys Met His
                80                  85                  90
Cys Ser Gly Glu His Tyr Glu Gly Lys Ile Ser Lys Thr Met Ser
                95                 100                 105
Gly Ile Glu Cys Gln Ser Trp Gly Ser Gln Ser Pro His Ala His
               110                 115                 120
Gly Tyr Leu Pro Ser Lys Phe Pro Asn Lys Asn Leu Lys Met Asn
               125                 130                 135
Tyr Cys Arg Asn Pro Asp Gly Glu Pro Arg Pro Trp Cys Phe Thr
               140                 145                 150
Thr Asp Pro Asn Lys Arg Trp Glu Phe Cys Asp Ile Pro Arg Cys
               155                 160                 165
Thr Thr Pro Pro Pro Thr Ser Gly Pro Thr Tyr Gln Cys Leu Lys
               170                 175                 180
Gly Arg Gly Glu Asn Tyr Arg Gly Thr Val Ser Val Thr Ala Ser
               185                 190                 195
Gly His Thr Cys Gln Arg Trp Ser Ala Gln Ser Pro His Lys His
               200                 205                 210
Asn Arg Thr Pro Glu Asn Phe Pro Cys Lys Asn Leu Glu Glu Asn
               215                 220                 225
Tyr Cys Arg Asn Pro Asp Gly Glu Thr Ala Pro Trp Cys Tyr Thr
               230                 235                 240
Thr Asp Ser Glu Val Arg Trp Asp Tyr Cys Lys Ile Pro Ser Cys
               245                 250                 255
Gly Ser Ser Thr Thr Ser Thr Glu His Leu Asp Ala Pro Val Pro
               260                 265                 270
Pro Glu Gln Thr Pro Val Ala Gln Asp Cys Tyr Arg Gly Asn Gly
               275                 280                 285
Glu Ser Tyr Arg Gly Thr Ser Ser Thr Thr Ile Thr Gly Arg Lys
               290                 295                 300
Cys Gln Ser Trp Val Ser Met Thr Pro His Arg His Glu Lys Thr
               305                 310                 315
Pro Gly Asn Phe Pro Asn Ala Gly Leu Thr Met Asn Tyr Cys Arg
               320                 325                 330
Asn Pro Asp Ala Asp Lys Ser Pro Trp
               335                 339
```

( 2 ) INFORMATION FOR SEQ ID NO: 6:

( i ) SEQUENCE CHARACTERISTICS:
    ( A ) LENGTH: 339
    ( B ) TYPE: amino acid
    ( D ) TOPOLOGY: linear ( x i ) SEQUENCE DESCRIPTION: SEQ ID NO: 6:

```
Ile Tyr Leu Leu Glu Cys Lys Thr Gly Asn Gly Gln Thr Tyr Arg
 1               5                  10                  15
Gly Thr Thr Ala Glu Thr Lys Ser Gly Val Thr Cys Gln Lys Trp
                20                  25                  30
Ser Ala Thr Ser Pro His Val Pro Lys Phe Ser Pro Glu Lys Phe
                35                  40                  45
Pro Leu Ala Gly Leu Glu Glu Asn Tyr Cys Arg Asn Pro Asp Asn
                50                  55                  60
Asp Glu Asn Gly Pro Trp Cys Tyr Thr Thr Asp Pro Asp Lys Arg
                65                  70                  75
Tyr Asp Tyr Cys Asp Ile Pro Glu Cys Glu Asp Lys Cys Met His
                80                  85                  90
Cys Ser Gly Glu Asn Tyr Glu Gly Lys Ile Ala Lys Thr Met Ser
                95                  100                 105
Gly Arg Asp Cys Gln Ala Trp Asp Ser Gln Ser Pro His Ala His
                110                 115                 120
Gly Tyr Ile Pro Ser Lys Phe Pro Asn Lys Asn Leu Lys Met Asn
                125                 130                 135
Tyr Cys Arg Asn Pro Asp Gly Glu Pro Arg Pro Trp Cys Phe Thr
                140                 145                 150
Thr Asp Pro Gln Lys Arg Trp Glu Phe Cys Asp Ile Pro Arg Cys
                155                 160                 165
Thr Thr Pro Pro Pro Ser Ser Gly Pro Lys Tyr Gln Cys Leu Lys
                170                 175                 180
Gly Thr Gly Lys Asn Tyr Gly Gly Thr Val Ala Val Thr Glu Ser
                185                 190                 195
Gly His Thr Cys Gln Arg Trp Ser Glu Gln Thr Pro His Lys His
                200                 205                 210
Asn Arg Thr Pro Glu Asn Phe Pro Cys Lys Asn Leu Glu Glu Asn
                215                 220                 225
Tyr Cys Arg Asn Pro Asp Gly Glu Lys Ala Pro Trp Cys Tyr Thr
                230                 235                 240
Thr Asn Ser Glu Val Arg Trp Glu Tyr Cys Thr Ile Pro Ser Cys
                245                 250                 255
Glu Ser Ser Pro Leu Ser Thr Glu Arg Met Asp Val Pro Val Pro
                260                 265                 270
Pro Glu Gln Thr Pro Val Pro Gln Asp Cys Tyr His Gly Asn Gly
                275                 280                 285
Gln Ser Tyr Arg Gly Thr Ser Ser Thr Thr Ile Thr Gly Arg Lys
                290                 295                 300
Cys Gln Ser Trp Ser Ser Met Thr Pro His Arg His Leu Lys Thr
                305                 310                 315
Pro Glu Asn Tyr Pro Asn Ala Gly Leu Thr Met Asn Tyr Cys Arg
                320                 325                 330
Asn Pro Asp Ala Asp Lys Ser Pro Trp
                335                 339
```

We claim:

1. A method of inhibiting angiogenesis in a mammal, comprising administering to the mammal an effective amount of angiostatin protein, wherein the angiostatin protein contains approximately kringle regions 1 through 4 of a plasminogen molecule and has anti-angiogenic activity.

2. The method of claim 1, wherein the angiostatin protein has a molecular weight of between approximately 38 kilodaltons and 45 kilodaltons as determined by reducing polyacrylamide gel electrophoresis.

3. The method of claim 1, wherein the angiostatin protein has an amino-terminal amino acid sequence beginning at approximately amino acid 98 of a plasminogen molecule.

4. The method of claim 1, wherein the angiostatin protein has a beginning amino acid sequence selected from the group consisting of SEQ ID NO: 2, SEQ ID NO: 3, SEQ ID NO: 4, SEQ ID NO: 5, and SEQ ID NO: 6.

5. The method of claim 1, wherein the angiostatin protein has endothelial cell proliferation inhibiting activity.

6. The method of claim 1, wherein the mammal has a disease or condition mediated by angiogenesis.

7. The method of claim 1, wherein the mammal has a cancer.

8. A method of inhibiting endothelial cell proliferation, comprising administering to an endothelial cell an effective amount of angiostatin protein, wherein the angiostatin protein contains approximately kringle regions 1 through 4 of a plasminogen molecule and has endothelial cell proliferation inhibiting activity.

9. The method of claim 8, wherein the angiostatin protein has a molecular weight of between approximately 38 kilodaltons and 45 kilodaltons as determined by reducing polyacrylamide gel electrophoresis.

10. The method of claim 8, wherein the angiostatin protein has an amino-terminal amino acid sequence beginning at approximately amino acid 98 of a plasminogen molecule.

11. The method of claim 8, wherein the angiostatin protein has a beginning amino acid sequence selected from the group consisting of SEQ ID NO: 2, SEQ ID NO: 3, SEQ ID NO: 4, SEQ ID NO: 5, and SEQ ID NO: 6.

12. The method of claim 8, wherein the angiostatin protein has anti-angiogenic activity.

13. The method of claim 8, wherein the endothelial cell is in a mammal.

14. The method of claim 13, wherein the mammal has a disease or condition mediated by angiogenesis.

15. The method of claim 13, wherein the mammal has a cancer.

* * * * *

UNITED STATES PATENT AND TRADEMARK OFFICE
CERTIFICATE OF CORRECTION

PATENT NO. : 5,733,876

DATED : March 31, 1998

INVENTOR(S) : Michael S. O'Reilly and M. Judah Folkman

It is certified that error appears in the above-indentified patent and that said Letters Patent is hereby corrected as shown below:

Please add the following text on page 1, column 1, line 2:

"This invention was made with government support under National Institutes of Health grant P01-CA45548. The United States Government may have certain rights in this invention."

Signed and Sealed this

Thirtieth Day of June, 1998

Attest:

BRUCE LEHMAN

Attesting Officer

Commissioner of Patents and Trademarks